United States Patent
Deak et al.

(10) Patent No.: US 12,066,401 B2
(45) Date of Patent: Aug. 20, 2024

(54) HYDROGEN GAS SENSOR UTILIZING ELECTRICALLY ISOLATED TUNNELING MAGNETORESISTIVE STRESS SENSING ELEMENTS

(71) Applicant: MultiDimension Technology Co., Ltd., Zhangjiagang (CN)

(72) Inventors: James Geza Deak, Zhangjiagang (CN); Zhimin Zhou, Zhangjiagang (CN)

(73) Assignee: MultiDimension Technology Co., Ltd., Zhangjiagang (CN)

( * ) Notice: Subject to any disclaimer, the term of this patent is extended or adjusted under 35 U.S.C. 154(b) by 200 days.

(21) Appl. No.: 17/755,180

(22) PCT Filed: Oct. 27, 2020

(86) PCT No.: PCT/CN2020/123946
§ 371 (c)(1),
(2) Date: Apr. 22, 2022

(87) PCT Pub. No.: WO2021/083137
PCT Pub. Date: May 6, 2021

(65) Prior Publication Data
US 2022/0373513 A1   Nov. 24, 2022

(30) Foreign Application Priority Data
Oct. 30, 2019   (CN) .......................... 201911048138.8

(51) Int. Cl.
*G01N 27/72*   (2006.01)
*G01N 33/00*   (2006.01)

(52) U.S. Cl.
CPC ........... *G01N 27/72* (2013.01); *G01N 33/005* (2013.01)

(58) Field of Classification Search
CPC .............................. G01N 27/72; G01N 33/005
See application file for complete search history.

(56) References Cited

U.S. PATENT DOCUMENTS 9,817,084 B2   11/2017   Deak
10,082,484 B2   9/2018   Breuer et al.
(Continued)

FOREIGN PATENT DOCUMENTS

CN   102565727 A   7/2012
CN   102692287 A   9/2012
(Continued)

OTHER PUBLICATIONS

English translation of CN 102692287 accessed from iq.ip.com.*
(Continued)

*Primary Examiner* — Kristina M Deherrera
*Assistant Examiner* — Jean F Morello
(74) *Attorney, Agent, or Firm* — Schwegman Lundberg & Woessner, P.A.

(57) ABSTRACT

A hydrogen gas sensor utilizing electrically isolated tunneling magnetoresistive stress sensing elements is disclosed. The hydrogen gas sensor comprises: a deformable substrate, a magnetoresistive bridge stress sensor located on the deformable substrate, an electrical isolation layer covering the magnetoresistive bridge stress sensor, a magnetic shielding layer located on the electrical isolation layer, and a hydrogen sensing layer located above the deformable substrate. The hydrogen sensing layer is located in a plane perpendicular to the deformation of the substrate covering the electrical isolation layer. The hydrogen sensing layer is used for absorbing or desorbing hydrogen gas to generate expansion or contraction deformation and cause a stress change of the deformable substrate. The magnetoresistive bridge stress sensor is used for measuring a hydrogen gas concentration utilizing the stress change of the deformable substrate. It results in a hydrogen gas sensor with improved performance.

13 Claims, 8 Drawing Sheets

(56) References Cited

U.S. PATENT DOCUMENTS

| | | |
|---|---|---|
| 2015/0091560 A1 | 4/2015 | Deak et al. |
| 2016/0109535 A1 | 4/2016 | Deak |
| 2017/0082581 A1 | 3/2017 | Breuer et al. |
| 2017/0343522 A1 | 11/2017 | Ikehashi et al. |
| 2019/0025385 A1 | 1/2019 | Breuer et al. |
| 2019/0162694 A1 | 5/2019 | Hayashi |
| 2019/0346406 A1* | 11/2019 | Gerber .................. G01R 33/07 |

FOREIGN PATENT DOCUMENTS

| | | |
|---|---|---|
| CN | 103267955 | 8/2013 |
| CN | 106546644 A | 3/2017 |
| CN | 109839411 A | 6/2019 |
| CN | 110646502 A | 1/2020 |
| CN | 211043234 U | 7/2020 |
| WO | WO-2021083137 A1 | 5/2021 |

OTHER PUBLICATIONS

"International Application No. PCT/CN2020/123946, International Search Report and Written Opinion mailed Jan. 27, 2021", (Jan. 27, 2021), 13 pgs.

* cited by examiner

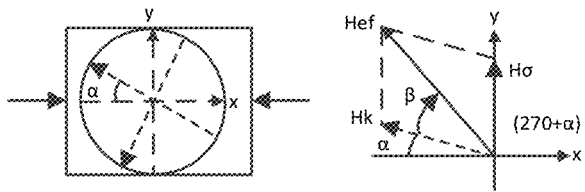
FIG.9N
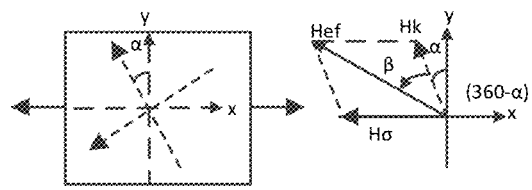
FIG.9O
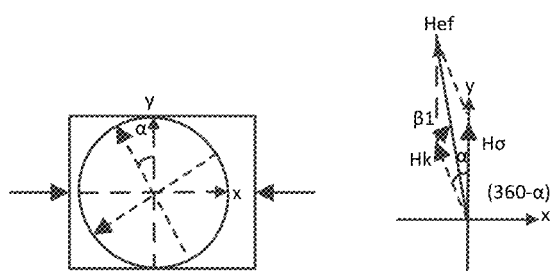
FIG.9P
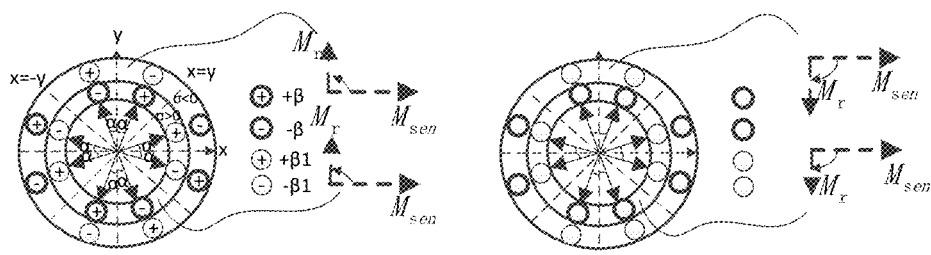
FIG.10A  FIG.10B
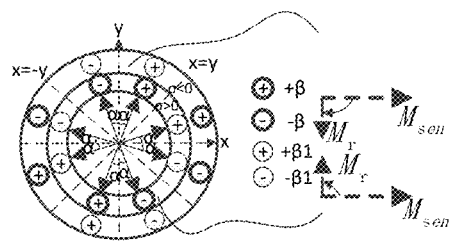
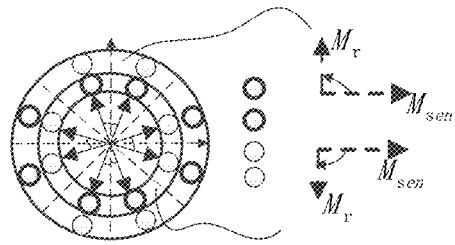
FIG.10C  FIG.10D

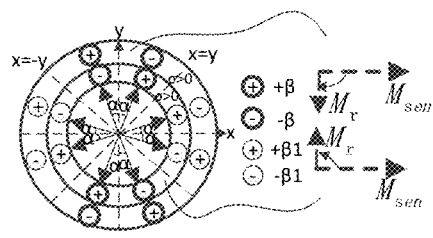
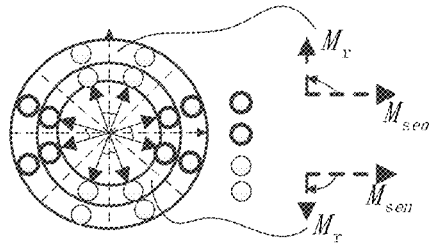
FIG.15E  FIG.15F
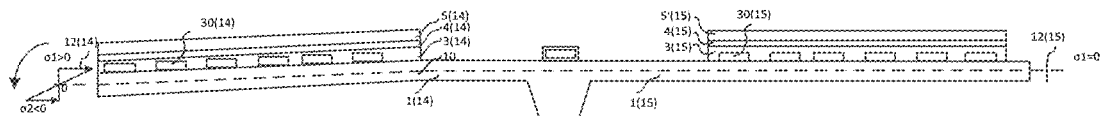
FIG.16
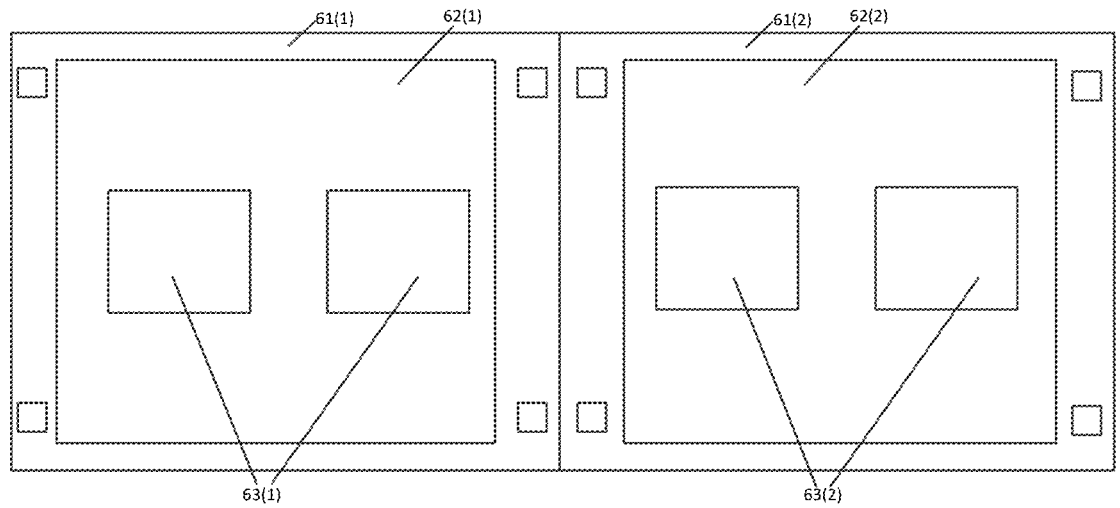
FIG.17
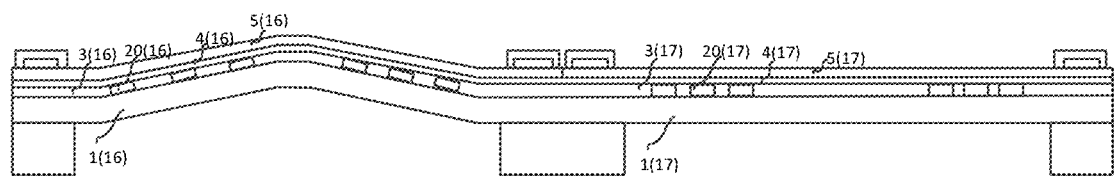
FIG.18
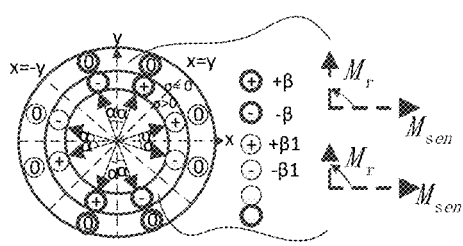
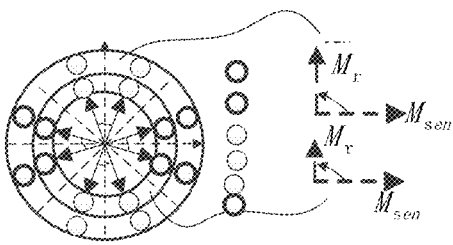
FIG.19A  FIG.19B

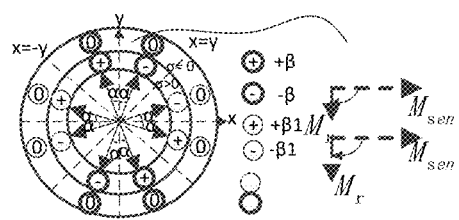
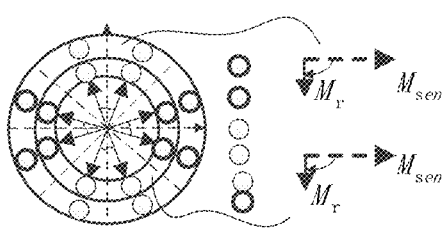
FIG.19C　　　　　　　　　　　　　　　FIG.19D
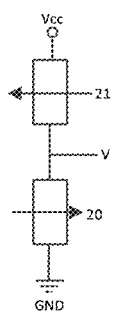
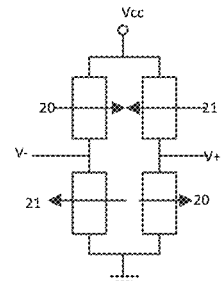
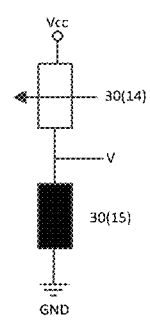
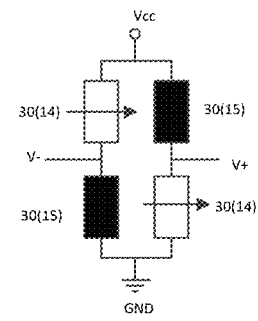
FIG.20A　　　　FIG.20B　　　　FIG.20C　　　　FIG.20D

HYDROGEN GAS SENSOR UTILIZING ELECTRICALLY ISOLATED TUNNELING MAGNETORESISTIVE STRESS SENSING ELEMENTS

PRIORITY CLAIM TO RELATED APPLICATIONS

This application is a U.S. national stage filing under 35 U.S.C. § 371 from International Application No. PCT/CN2020/123946, filed on 27 Oct. 2020, which claims priority to Chinese Application No. 201911048138.8, filed on 30 Oct. 2019. This application incorporates by reference the entirety of International Application No. PCT/CN2020/123946 and its published version WO2021/083137 (published 06 May 2021).

TECHNICAL FIELD

Embodiments of the present disclosure relate to gas sensor technologies, and more particularly, to a hydrogen gas sensor utilizing electrically isolated tunneling magnetoresistive stress sensing elements.

BACKGROUND ART

As a renewable new energy without harmful emissions, hydrogen gas can be used as an alternative to fossil fuel energy. It has attracted more and more attention worldwide in recent years and is undergoing rapid development. At present, the world's major economies, such as the United States, the European Union, and Japan, are sparing no effort to promote hydrogen gas as a new energy and new fuel for future vehicles and households. Toyota and other companies have begun to design and produce hydrogen fuel vehicles.

Hydrogen gas cannot be perceived by human sense organs, but it is highly flammable and explosive, with a threshold of flammability in air around 4%. In order to ensure the safety of hydrogen gas powered equipment, reliable and highly sensitive hydrogen gas sensors are needed.

There are many kinds of conventional hydrogen gas sensors, but many of them have disadvantages such as being complex utilizing optical measurement methods, poor hydrogen gas concentration measuring range, low in sensitivity, slow response time, and so on. In addition, for many existing sensors work, there are electric currents and voltages in the sensing units, that when the concentration of hydrogen gas in the air reaches the explosive limit, the gas may be ignited, which will result in an explosion.

SUMMARY OF THE INVENTION

Embodiments of the present disclosure provide a hydrogen gas sensor utilizing electrically isolated tunneling magnetoresistive stress sensing elements to improve the performance of hydrogen gas sensors.

The embodiments of the present disclosure provide a hydrogen gas sensor utilizing electrically isolated tunneling magnetoresistive stress sensing elements, including: a deformable substrate;

a magnetoresistive bridge stress sensor located on the deformable substrate, an electrical isolation layer covering the magnetoresistive bridge stress sensor, and a magnetic shielding layer located on the electrical isolation layer; and a hydrogen sensing layer located above the deformable substrate, where the hydrogen sensing layer is located in a plane perpendicular to the deformation of the substrate covering the electrical isolation layer, the hydrogen sensing layer is used for absorbing or desorbing hydrogen gas to generate expansion or contraction deformation and thus cause a stress change of the deformable substrate, and the magnetoresistive bridge stress sensor is used for measuring a hydrogen gas concentration utilizing the stress change of the deformable substrate.

In the embodiments of the present disclosure, the hydrogen gas sensor utilizing electrically isolated tunneling magnetoresistive stress sensing elements is provided. The hydrogen gas sensor comprises the deformable substrate, the tunneling magnetoresistive (TMR) bridge stress sensor located on the deformable substrate, the magnetic shielding layer located on the TMR bridge stress sensor, and the hydrogen sensing layer, where the hydrogen sensing layer is used for absorbing or desorbing hydrogen gas to generate expansion or contraction and thus cause a stress change of the deformable substrate, and the magnetoresistive bridge stress sensor is configured to collect stress signals and convert the same into electrical signals, thus realizing the measurement of hydrogen gas concentration in accordance with a relationship between the stress and the hydrogen gas concentration. In the embodiments, the deformable substrate can sensitively produce corresponding changes in real time in accordance with the change of the hydrogen sensing layer, which improves the sensitivity and response rate of the hydrogen gas sensor; and furthermore, the measurement method is simple. In addition, the electrical isolation between the hydrogen gas environment and the magnetoresistive bridge stress sensor can be realized in the presence of the electrical isolation layer, so that the safety is guaranteed; and the hydrogen gas sensor can also be used in an environment with a high hydrogen gas concentration, thus enlarging the measurement range. It results in a hydrogen gas sensor with improved performance.

BRIEF DESCRIPTION OF THE DRAWINGS

To more clearly illustrate the technical solution in the embodiments of the present disclosure and the prior art, the drawings required in the description of the embodiments and the prior art are briefly described below; and it is apparent to those of ordinary skill in the art that the drawings are merely some embodiments of the present disclosure, and other drawings may also be obtained according to these drawings without creative labor.

FIGS. 10A-10D are circumferential distribution diagrams of initial magnetic moment angles and rotation angles of the free layers under the action of the tensile stress and the compressive stress;

FIGS. 15A-15F are circumferential distribution diagrams of the initial magnetic moment angles and the rotation angles of the free layers under the action of the tensile stress and the compressive stress;

FIG. 16 is a schematic diagram of a reference magnetoresistive bridge stress sensor as well as its structure and stress distribution on the cantilever beam provided by the embodiments of the present disclosure;

FIG. 17 is a schematic diagram of the reference magnetoresistive bridge stress sensor as well as its structure and stress distribution on the membrane assembly provided by the embodiments of the present disclosure;

FIG. 18 is a schematic diagram of the reference magnetoresistive bridge stress sensor as well as its structure and stress distribution on the membrane assembly provided by the embodiments of the present disclosure;

FIGS. 19A-19D are circumferential distribution diagrams of the initial magnetic moment angles and the rotation angles of the free layers under the action of reference tensile and compressive stresses; and FIGS. 20A-20D are schematic diagrams of bridge structures of the magnetoresistive bridge stress sensor.

DETAILED DESCRIPTION

To make the objective, technical solution, and advantages of the embodiments of the present disclosure clearer, the technical solution in the embodiments of the present disclosure will be clearly and completely described below with reference to the drawings in the embodiments of the present disclosure. It is obvious that the described embodiments are part, but not all, of the embodiments of the present disclosure. Based on the embodiments of the present disclosure, all other embodiments obtained by those of ordinary skill in the art without creative labor shall fall within the protection scope of the present disclosure.

Figure 1:
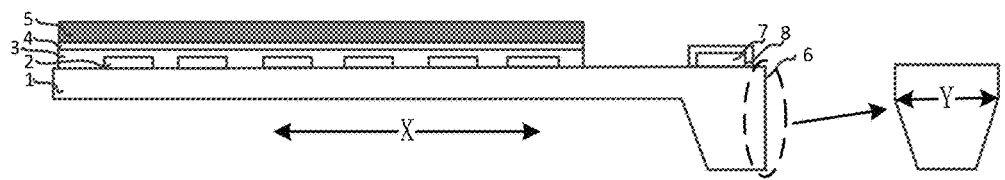
FIG. 1 is a schematic diagram of a hydrogen gas sensor provided by the embodiments of the present disclosure.

Referring to FIG. 1, a hydrogen gas sensor utilizing electrically isolated tunneling magnetoresistive stress sensing elements is provided by an embodiment of the present disclosure. The hydrogen gas sensor provided by this embodiment includes: a deformable substrate 1, a magnetoresistive bridge stress sensor 2 located on the deformable substrate 1, an electrical isolation layer 3 covering the magnetoresistive bridge stress sensor 2, a magnetic shielding layer 4 located on the electrical isolation layer 3, and a hydrogen sensing layer 5 located above the deformable substrate 1. The hydrogen sensing layer 5 is located in a plane perpendicular to the deformation of the substrate 1 covering the electrical isolation layer 3. The hydrogen sensing layer 5 is used for absorbing or desorbing hydrogen gas to generate expansion or contraction deformation and cause a stress change of the deformable substrate 1. The magnetoresistive bridge stress sensor 2 is used for measuring a hydrogen gas concentration utilizing the stress change of the deformable substrate 1.

According to the embodiment, the deformable substrate 1 can optionally be any kind of deformable film layer or substrate, where the deformable substrate 1 is in a planar state in an original state, and the deformable substrate 1 is deformed and produces a stress change in a deformed state. Optionally, the deformable substrate 1 is a cantilever beam; or, the deformable substrate is a membrane assembly, the membrane assembly includes a frame and a membrane enclosed in the frame, and the magnetoresistive bridge stress sensor is disposed on the membrane.

According to the embodiment, the deformable substrate 1 is provided with the magnetoresistive bridge stress sensor 2, the magnetoresistive bridge stress sensor 2 includes magnetoresistance sensor units, and the magnetoresistive bridge stress sensor 2 is covered with the electrical isolation layer 3 and the magnetic shielding layer 4 located on the electrical isolation layer 3. The electrical isolation layer 3 is configured to realize the electrical insulation isolation between the power supply environment of the magnetoresistive bridge stress sensor 2 and the external environment, especially the isolation between a hydrogen gas environment and the power supply environment in case of a hydrogen gas environment, thus avoiding hydrogen gas explosion, and improving product testing safety. The magnetic shielding layer 4 can isolate the magnetic field of the external environment from the magnetoresistive bridge stress sensor 2 to avoid the influence of the magnetic field of the external environment on the magnetoresistive bridge stress sensor 2, so that the magnetoresistive bridge stress sensor 2 mainly collects the deformation signals of the deformable substrate 1, and the testing accuracy of the magnetoresistive bridge stress sensor 2 is accordingly improved. Optionally, the magnetoresistive bridge stress sensor 2 is a tunneling magnetoresistive bridge stress sensor, the electrical isolation layer is optionally any kind of film layer that can realize electrical insulation, and the magnetic shielding layer is optionally any kind of film layer that can realize electromagnetic shielding.

According to the embodiment, the hydrogen sensing layer 5 is disposed above the deformable substrate 1; and optionally, as shown in FIG. 1, the hydrogen sensing layer 5 is attached to the magnetic shielding layer 4, and in other embodiments, the hydrogen sensing layer can also be optionally attached directly to the deformable substrate. The hydrogen sensing layer 5 is located in a plane perpendicular to the deformation of the substrate 1 covering the electrical isolation layer 3, and then the deformation of the deformable substrate 1 in the area covered by the hydrogen sensing layer can be caused by the deformation of the hydrogen sensing layer 5 absorbing or desorbing hydrogen gas, so that the magnetoresistive bridge stress sensor 2 located in the area covered by the hydrogen sensing layer can perform hydrogen gas concentration measurement according to the stress change of the deformable substrate 1. The hydrogen sensing layer 5 will undergo expansion deformation when absorbing hydrogen gas and undergo contraction deformation when desorbing hydrogen gas. Optionally, the hydrogen sensing layer is made of non-Pd hydrogen storage metals or alloys, thus being capable of reacting with hydrogen gas to form hydrides, which results in an increase in the lattice constant, volume, and length. When a membrane structure is formed by the hydrogen sensing layer together with a substrate, a tensile stress can be formed on the surface, which is contacted with the hydrogen sensing layer, of the substrate, and a compressive stress can be formed on the surface, that is not contacted with the hydrogen sensing layer, of the substrate. Optionally, the hydrogen sensing layer includes at least one of $AB_5$, $AB_3$, $AB_2$, AB and $A_2B$ type intermetallic compounds, where A represents a strong metal hydride forming element and B represents a transition metal element. Optionally, A includes rare earth metals, Ca, Mg, Zr, or Ti, and B includes Ni, Co, Fe, Mn, or Cr.

As shown in FIG. 1, optionally, the magnetoresistive bridge stress sensor 2 may be located on the upper surface of the deformable substrate 1. In other embodiments, the magnetoresistive bridge stress sensor can optionally be located on the lower surface of the deformable substrate, or in other embodiments, the magnetoresistive bridge stress sensor can also optionally be distributed on both the upper and lower surfaces of the deformable substrate at the same time. It is understandable that no matter the magnetoresistive bridge stress sensor is disposed on the surface(s) at one side or both sides of the deformable substrate, the magnetoresistive bridge stress sensor is provided with the electrical isolation layer and the magnetic shielding layer that are stacked in sequence.

Optionally, the magnetoresistive bridge stress sensor 2 is provided with an electrical transmission port assembly 7, and the electrical transmission port assembly 7 is directly connected with the deformable substrate 1 and is sealed on the deformable substrate 7 by means of sealant 8, where the deformable substrate 7 includes the substrate 6, the electrical transmission port assembly 7 includes various ports such as a power port, a grounding port, and an output port of the magnetoresistive bridge stress sensor 2, and the electrical transmission port assembly 7 is located above the substrate 6 and is sealed by the sealant 8. The corresponding relationship between stresses and hydrogen gas concentrations will be deduced and described by formulas below.

In a hydrogen gas atmosphere, the hydrogen sensing layer 5 will absorb hydrogen gas and become a metal hydride, and its volume and length will expand or elongate; and in a non-hydrogen gas atmosphere, the hydride in the hydrogen sensing layer 5 will release hydrogen gas and thus be reduced to metal and alloy, so that the volume and length of the hydrogen sensing layer 5 return to the original state. The characteristic of the hydrogen sensing layer 5 absorbing or desorbing hydrogen gas is similar to the thermal expansion and cold contraction of materials. A hydrogen expansion coefficient γ can be defined for the hydrogen sensing layer 5. The relationship between the hydrogen expansion coefficient γ and the hydrogen sensing layer 5 is similar to that between a thermal expansion coefficient and a material. The hydrogen expansion coefficient γ represents the characteristic of the hydrogen sensing layer 5 absorbing or desorbing hydrogen gas, and the expression (1) of the hydrogen expansion coefficient γ is:

$$\gamma = \frac{1}{L}\frac{dl}{dc}, \qquad (1)$$

where L is the original length of the hydrogen sensing layer, and c is the hydrogen gas concentration. Obviously, the hydrogen expansion coefficient γ is a function of the hydrogen gas concentration c, and is proportional to the hydrogen gas concentration c.

Figure 2:
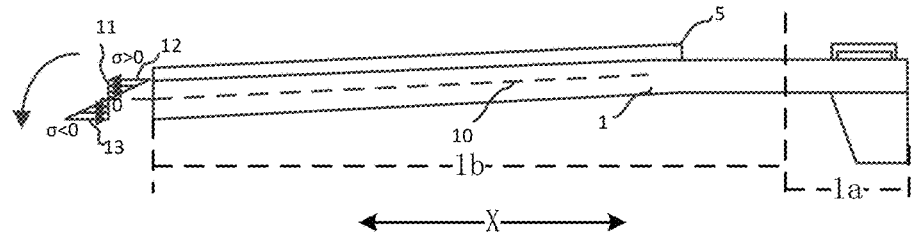
FIG. 2 is a schematic diagram of the structure and stress distribution of a hydrogen sensing layer and a cantilever beam provided by the embodiments of the present disclosure.
Figure 3:
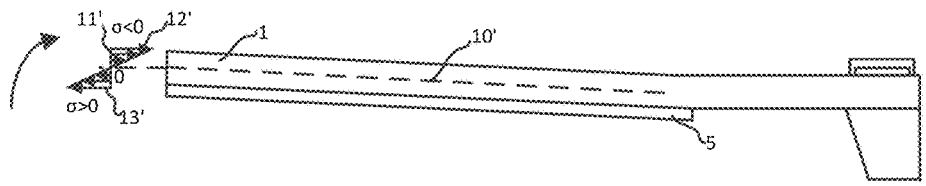
FIG. 3 is a schematic diagram of the structure and stress distribution of the hydrogen sensing layer and the cantilever beam provided by the embodiments of the present disclosure.

FIGS. 2 and 3 are schematic diagrams showing the deformation of the hydrogen sensing layer and the stress distribution of the deformable substrate. Optionally, the deformable substrate 1 is a cantilever beam, and the cantilever beam 1 includes a fixed part 1a and a free part 1b disposed at one side of the fixed part 1a, the extension direction of the free part 1b is the X-axis direction, and the magnetoresistive bridge stress sensor 2 is disposed at the free part 1b of the cantilever beam 1. A double-layer structure is formed by the hydrogen sensing layer 5 and the cantilever beam 1, where the double layers here mean that the hydrogen sensing layer 5 and the cantilever beam 1 directly or indirectly form the double-layer structure. The deformation of the hydrogen sensing layer 5 is constrained by the cantilever beam 1.

As shown in FIG. 2, the hydrogen sensing layer 5 is located on the upper surface of the cantilever beam 1, and expands and deforms by absorbing hydrogen gas, resulting in the deformation of the free part 1b of the cantilever beam 1 and the change of the internal stress on a cross section 11 of the cantilever beam 1. The free part 1b of the cantilever beam 1 will bend downward, and the upper surface of the cantilever beam 1 will generate a stretching stress (also called a tensile stress) 12, and the lower surface of the cantilever beam 1 will generate a compressive stress 13, where a plane 10 within the cantilever beam 1 corresponds to a zero-strain plane within the cross section 11.

As shown in FIG. 3, the hydrogen sensing layer 5 is located on the lower surface of the cantilever beam 1, and expands and deforms by absorbing hydrogen gas, resulting in the deformation of the free part lb of the cantilever beam 1 and the change of the internal stress on a cross section 11' of the cantilever beam 1. The free part 1b of the cantilever beam 1 will bend upward, and the upper surface of the cantilever beam 1 will generate a compressive stress 12', and the lower surface of the cantilever beam 1 will generate a tensile stress 13', where a plane 10' within the cantilever beam 1 corresponds to a zero-strain plane within the cross section 11'.

The stresses are σ, the tensile stress σ is greater than 0, and the compressive stress σ is less than 0. The tensile stress can be characterized as the stretching stress by the hydrogen sensing layer on the surface of the deformable substrate, or the stretching stress by the surface of the deformable substrate on the hydrogen sensing layer, and the compressive stress can be characterized as a compression stress by the hydrogen sensing layer on the surface of the deformable substrate, or a compression stress by the surface of the deformable substrate on the hydrogen sensing layer. Since the deformation of the hydrogen sensing layer 5 is constrained by the cantilever beam 1, the stress σ generated by the cantilever beam 1 in the hydrogen sensing layer 5 can be expressed by the following formula:

$$\sigma_f \frac{1}{6C} \frac{E_S d_S^2}{(1-v_s)d_f}, \quad (2)$$

where Es is a Young's modulus of the cantilever beam, ds is a thickness of the cantilever beam, C is a bending radius of the cantilever beam, Vs is a poisson's ratio of the cantilever beam, σf is the internal stress of the hydrogen sensing layer, and $d_f$ is a thickness of the hydrogen sensing layer.

On the other hand, the stress σ in the hydrogen sensing layer 5 can also be expressed in terms of the hydrogen expansion coefficient γ as follows:

$$\sigma_f = \frac{E_f}{1-v_f}(-\gamma)\Delta c \quad (3)$$

where $E_f$ is a Young's modulus of the hydrogen sensing layer, and $V_f$ is a poisson's ratio of the hydrogen sensing layer.

Therefore, the stresses σ are proportional to the hydrogen gas concentration c, and the hydrogen gas concentration can be obtained by the magnetoresistive bridge stress sensor based on the stresses σ measured thereby.

Figure 4:
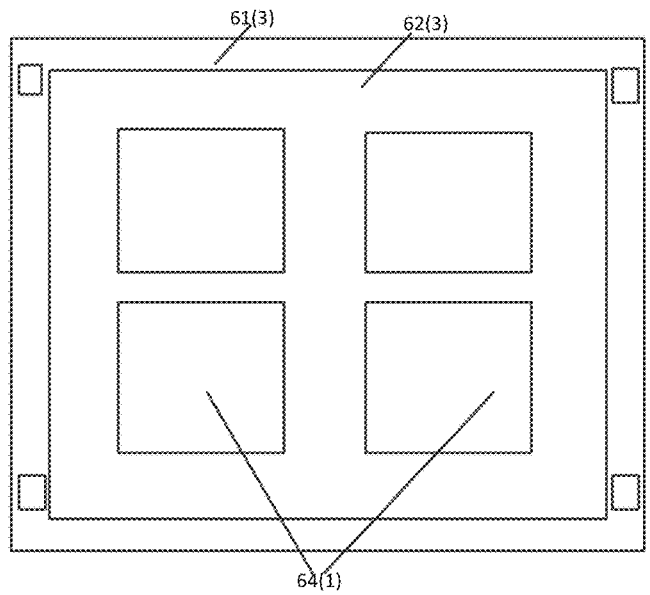
FIG. 4 is a structure and stress distribution diagram of the hydrogen sensing layer and a membrane assembly provided by the embodiments of the present disclosure.

FIG. 4 is a schematic diagram showing the deformation of the hydrogen sensing layer and the stress distribution of the deformable substrate. Optionally, the deformable substrate 1 is a membrane assembly; and the membrane assembly includes a frame 61 (3) and a membrane 62 (3) enclosed in the frame 61 (3), and the magnetoresistive bridge stress sensor is disposed on the membrane 62 (3). Optionally, the magnetoresistive bridge stress sensor is located on either the upper or lower surface of the membrane 62 (3), or on both the upper and lower surfaces of the membrane 62 (3) at the same time. The magnetoresistive bridge stress sensor includes a plurality of magnetoresistance sensor units 64 (1). Under the action of the residual stress of the film layers on the membrane 62 (3), the membrane 62 (3) coated with the multiple film layers will deflect. Although this deformation is very small, the curvature radius of the deflection can be measured by a laser interferometer or a profilometer. The degree of deflection on the membrane 62 (3) reflects the magnitude of the residual stress of the multi-film layers, where the multi-film layers specifically refer to the collection of the film layers formed on the membrane. Similarly, the stress formula is as follows:

$$\sigma_f = \left(\frac{E}{1-v}\right)_s \frac{t_s^2}{6rt_f}$$

where $t_s$ and $t_f$ correspond to the thicknesses of the film layer and the membrane respectively, and r is the curvature radius; and E and v are respectively an elastic modulus and a poisson's ratio of the membrane.

Similarly, the stresses in the hydrogen sensing layer on the membrane are also proportional to the hydrogen expansion coefficient γ, which can be expressed by the following formula:

$$\sigma_f \propto \frac{E_f}{1-v_f}(-\gamma)\Delta c$$

where $E_f$ is the Young's modulus of the hydrogen sensing layer, and $V_f$ is the poisson's ratio of the hydrogen sensing layer.

Therefore, the stresses σ are proportional to the hydrogen gas concentration c, and the hydrogen gas concentration can be obtained by the magnetoresistive bridge stress sensor based on the stresses σ measured thereby.

As mentioned above, for both the cantilever beam and the membrane assembly, the substrate is coated with the hydrogen sensing layer. After absorbing hydrogen gas, the hydrogen sensing layer undergoes extension or contraction deformation in volume and length. In this way, the stress change of the hydrogen sensing layer is constrained by the substrate, which causes the stress and deflection changes of the substrate, so the directions and magnitudes of the stresses generated on the membrane and the surfaces of the cantilever beam have a similar relationship. It can be understood that the substrate of the cantilever beam is the beam body, and the substrate of the membrane assembly is the membrane. As shown in the above drawings, the difference between the cantilever beam and the membrane assembly is that the cantilever beam has a fixed end, while the membrane is fixed on all sides.

In the embodiments of the present disclosure, the hydrogen gas sensor utilizing electrically isolated tunneling magnetoresistive stress sensing elements is provided. The hydrogen gas sensor includes the deformable substrate, the tunneling magnetoresistive (TMR) bridge stress sensor located on the deformable substrate, the magnetic shielding layer located on the TMR bridge stress sensor, and the hydrogen sensing layer, where the hydrogen sensing layer is used for absorbing or desorbing hydrogen gas to generate expansion or contraction and thus cause the stress change of the deformable substrate, and the magnetoresistive bridge stress sensor is configured to collect stress signals and convert the same into electrical signals, thus realizing the measurement of hydrogen gas concentration in accordance with a relationship between the stress and the hydrogen gas concentration. In the embodiment, the deformable substrate can sensitively produce corresponding changes in real time in accordance with the change of the hydrogen sensing layer, which improves the sensitivity and response rate of the hydrogen gas sensor; and furthermore, the measurement method is simple. In addition, the electrical isolation between the hydrogen gas environment and the magnetoresistive bridge stress sensor can be realized in the presence of the electrical isolation layer, so that the safety is guaranteed; and the hydrogen gas sensor can also be used in an environment with a high hydrogen gas concentration, thus enlarging the measurement range. It results in a hydrogen gas sensor with improved performance.

Figure 5:
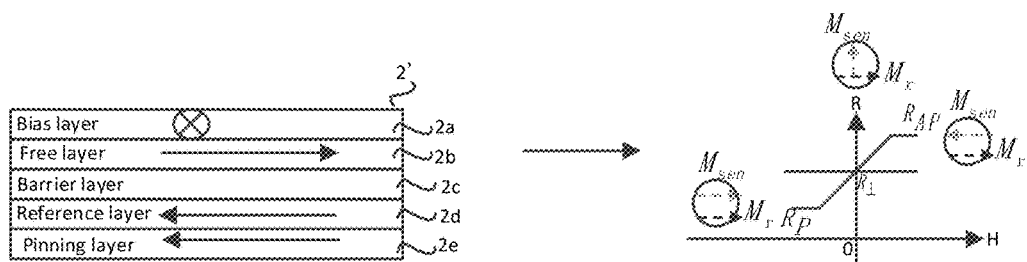
FIG. 5 is a schematic diagram of a stacked structure of magnetoresistance sensor units as described in the embodiments of the present disclosure.

In one exemplary embodiment, on the basis of the above technical solution, optionally, as shown in FIG. 5, the length direction of the deformable substrate is the X-axis direction, and the width direction of the deformable substrate is the Y-axis direction; and the magnetoresistive bridge stress sensor includes a plurality of magnetoresistance sensor units, each of which includes a multi-film layer stacked structure 2' parallel to a plane X-Y, and the multi-film layer 2' at least includes a pinning layer 2e, a reference layer 2d, a barrier layer 2c, a free layer 2b, and a bias layer 2a that are stacked in sequence.

Referring to FIG. 1, a side view of the cantilever beam and a front view of the fixed part are shown, where the X-axis direction is parallel to the length direction of the cantilever beam, and the Y-axis direction is parallel to the width direction of the cantilever beam, i.e., the width direction of the fixed part; and the plane X-Y is a plane formed by the X-axis direction and the Y-axis direction. Specifically, when the surface, where the magnetoresistive bridge stress sensor is disposed, of the deformable substrate is a long strip, for example, the deformable substrate is the cantilever beam, the long side direction of the long strip is the length direction of the deformable substrate, i.e., the X-axis direction, and the short side direction of the long strip is the width direction of the deformable substrate, i.e., the Y-axis direction. When the surface, where the magnetoresistive bridge stress sensor is disposed, of the deformable substrate is a square, for example, the deformable substrate is the membrane assembly, and the membrane is square, the adjacent two sides of the square are the length direction and width direction of the deformable substrate, i.e., the X-axis direction and the Y-axis direction. Alternatively, the magnetoresistive bridge stress sensor is disposed on the surface of the deformable substrate, and the arrangement direction of the magnetoresistance sensor units in the magnetoresistive bridge stress sensor is the longitudinal direction of the deformable substrate, i.e., the X-axis direction, and the extension direction of the magnetoresistance sensor units in the magnetoresistive bridge stress sensor is the width direction of the deformable substrate, i.e., the Y-axis direction.

FIG. 5 shows the multi-film layer stacked structure of the magnetoresistive bridge stress sensor. The magnetization direction of the reference layer 2d depends on the pinning layer 2e, and the bias direction of the free layer 2b depends on the bias layer 2a. Optionally, the free layer 2b is made of a magnetostriction material, such as CoFeB, CoFe, or NiFe, with a high positive magnetostriction coefficient (λs=30 ppm). The principle of a TMR stress sensor is to use the magnetostrictive effect of the free layer 2b to rotate the magnetic moment of the free layer 2b under the action of stresses, thereby making an angle a between the free layer 2b and the reference layer 2e change. The relationship between the resistances of the magnetoresistance sensor units and the angle α between the free layer 2b and the reference layer 2e is as follows:

$$R(\alpha) = \frac{R_\perp}{1 + \frac{R_{AP} - R_s}{R_{AP} + R_s}\cos(\phi)} \quad (4)$$

$R_{AP}$ and $R_P$, $R \perp$ represent the resistance values when φ is equal to 0°, 90° and 180°, respectively.

The deflection produced by stresses in the free layers is equivalent to an external magnetic field $H_\sigma$:

$$H_\sigma = \frac{3\sigma_f \lambda_s}{M_s} \quad (5)$$

where λs the magnetostriction coefficient, and $M_s$ is a saturation magnetization; when the tensile stress σ is greater than 0, $H_\sigma$ is located in the direction of the tensile stress σ; and when the compressive stress σ is less than 0, $H_\sigma$ is located in the direction perpendicular to the compressive stress σ.

In one exemplary embodiment, on the basis of the above technical solution, optionally, the deformable substrate has a first surface and a second surface which are arranged along the Z-axis direction; the magnetoresistive bridge stress sensor has a push-pull bridge structure, and includes the push magnetoresistance sensor units and the pull magnetoresistance sensor units; the push magnetoresistance sensor units are disposed on the first surface, and the pull magnetoresistance sensor units are disposed on the second surface; and the push magnetoresistance sensor units and the pull magnetoresistance sensor units bear stresses of the same magnitude and in the opposite directions. Optionally, the deformable substrate is the cantilever beam or the membrane assembly, its first surface and second surface are both parallel to the plane X-Y, and its Z-axis direction is perpendicular to the plane X-Y, where the push magnetoresistance sensor units and the pull magnetoresistance sensor units are respectively located on the two opposite surfaces of the deformable substrate, for example, the push magnetoresistance sensor units are located on the upper surface of the deformable substrate and the pull magnetoresistance sensor units are located on the lower surface of the deformable substrate, or, the push magnetoresistance sensor units are located on the lower surface of the deformable substrate and the pull magnetoresistance sensor units are located on the upper surface of the deformable substrate. The structure and working principle of the hydrogen gas sensor when utilizing the two optional types of deformable substrates alternatively are described in detail below.

Figure 6:
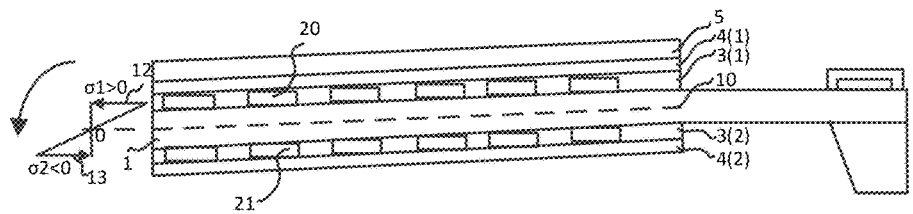
FIG. 6 is a schematic diagram of a push-pull magnetoresistive bridge stress sensor as well as its structure and stress distribution on the cantilever beam provided by the embodiments of the present disclosure.

FIG. 6 shows the push-pull magnetoresistive bridge stress sensor as well as its structure and stress distribution diagram on the cantilever beam. The hydrogen sensing layer 5 is located on the upper surface of the cantilever beam 1, the push magnetoresistance sensor units 20 and the pull magnetoresistance sensor units 21 are respectively located above and under the cantilever beam 1, the corresponding electrical isolation layer 3 (1) covers the surfaces of the push magnetoresistance sensor units 20, the electrical isolation layer 3 (2) covers the surfaces of the pull magnetoresistance sensor units 21, and the magnetic shielding layer 4 (1) and the magnetic shielding layer 4 (2) are located on the surfaces of the push magnetoresistance sensor units 20 and the pull magnetoresistance sensor units 21, respectively.

Assuming that the thickness df of the hydrogen sensing layer 5 is much less than the thickness ds of the cantilever beam 1, the zero-stress plane 10 is located at the middle position ds/2 of the cantilever beam 1, so the push magnetoresistance sensor units 20 and the pull magnetoresistance sensor units 21 bear stresses of the same magnitude and in the opposite directions. Optionally, the push magnetoresistance sensor units 20 are subjected to the tensile stress 12, and the tensile stress σ1 is greater than 0; the pull magnetoresistance sensor units 21 are subjected to the compressive stress 13, and the compressive stress σ2 is less than 0; and the tensile stress 12 and the compressive stress 13 are opposite in directions, but have the same magnitude, that is, σ1 is equal to −σ2.

In other embodiments, optionally, the hydrogen sensing layer may be located on the lower surface of the cantilever beam, or the hydrogen sensing layer may cover the upper parts of the pull magnetoresistance sensor units.

Figure 7:
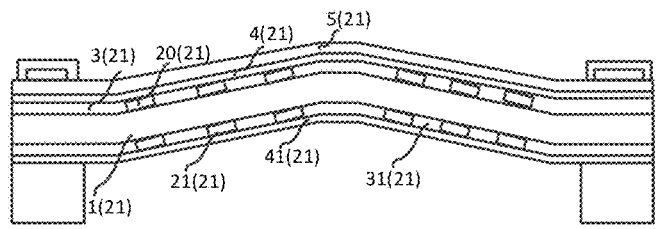
FIG. 7 is a schematic diagram of the push-pull magnetoresistive bridge stress sensor as well as its structure and stress distribution on the membrane assembly provided by the embodiments of the present disclosure.

FIG. 7 shows the push-pull magnetoresistive bridge stress sensor as well as its structure and stress distribution diagram on the membrane. The membrane assembly includes the peripheral frame (not shown) and the membrane 1 (21) defined by the peripheral frame. The hydrogen gas sensor also includes the push magnetoresistance sensor units 20

(21) and the electrical isolation layer 3 (21) which are located on the membrane 1 (21), the pull magnetoresistance sensor units 21 (21) and the electrical isolation layer 31 (21) that are located under the membrane 1 (21), the magnetic shielding layer 4 (21) located above the push magnetoresistance sensor units 20 (21), the magnetic shielding layer 41 (21) located above the pull magnetoresistance sensor units 21 (21), and the hydrogen sensing layer 5 (21) located on the magnetic shielding layer 4 (21); and at this point, the hydrogen sensing layer 5 (21) expands or elongates in volume after absorbing hydrogen gas, and the membrane will bend upward accordingly.

Assuming that the thickness of the hydrogen sensing layer is much less than the thickness of the membrane, the zero-stress plane is located in the middle of the membrane, so the push magnetoresistance sensor units and the pull magnetoresistance sensor units bear stresses of the same magnitude and in the opposite directions, that is, σ1 is equal to −σ2.

Figure 8:
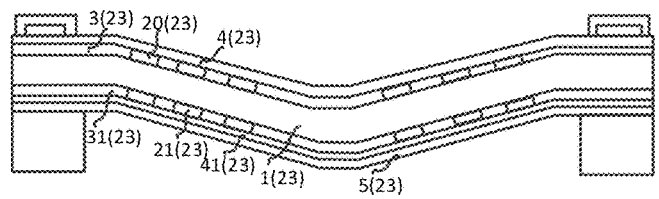
FIG. 8 is a schematic diagram of the push-pull magnetoresistive bridge stress sensor as well as its structure and stress distribution on the membrane assembly provided by the embodiments of the present disclosure.

FIG. 8 shows the push-pull magnetoresistive bridge stress sensor as well as its structure and stress distribution diagram on the membrane. The membrane assembly includes the peripheral frame (not shown) and the membrane 1 (23) defined by the peripheral frame. The hydrogen gas sensor also includes the push magnetoresistance sensor units 20 (23) and the electrical isolation layer 3 (23) which are located on the membrane 1 (23), the pull magnetoresistance sensor units 21 (23) and the electrical isolation layer 31 (23) that are located under the membrane 1 (23), the magnetic shielding layer 4 (23) located above the push magnetoresistance sensor units 20 (23), the magnetic shielding layer 41 (23) located above the pull magnetoresistance sensor units 21 (23), and the hydrogen sensing layer 5 (23) located on the magnetic shielding layer 41 (23); and at this point, the hydrogen sensing layer 5 (23) expands or elongates in volume after absorbing hydrogen gas, and the membrane will bend downward accordingly. Assuming that the thickness of the hydrogen sensing layer is much less than the thickness of the membrane, the zero-stress plane is located in the middle of the membrane, so the push magnetoresistance sensor units and the pull magnetoresistance sensor units bear stresses of the same magnitude and in the opposite directions, that is, σ1 is equal to −σ2.

Optionally, the angle at which the initial magnetic moment of the free layer of each push magnetoresistance sensor unit deviates from the Y-axis is α; when the magnetic moments of the free layers of the push magnetoresistance sensor units and the magnetic moments of the free layers of the pull magnetoresistance sensor units are simultaneously rotated clockwise or counterclockwise by the same angle to obtain the corresponding magnetic moments of the pinning layers, the angle at which the initial magnetic moment of the free layer of each pull magnetoresistance sensor unit deviates from the Y-axis is 90−α or 270−α; or, when the magnetic moments of the free layers of the push magnetoresistance sensor units and the magnetic moments of the free layers of the pull magnetoresistance sensor units are rotated in different directions and by the same angle, the angle at which the initial magnetic moment of the free layer of each pull magnetoresistance sensor unit deviates from the Y-axis is 90+α or 270+α; and the value range of a is from 0° to 360°, where when the free layers are made of a material with the positive magnetostriction coefficient and bear the tensile stress or made of a material with the negative magnetostriction coefficient and bear the compressive stress, α is not 0° or 180°, and when the free layers are made of a material with a positive magnetostriction coefficient and bear a compressive stress or made of a material with a negative magnetostriction coefficient and bear a tensile stress, α is not 90° or 270°. It should be noted that the symbols and numerical values of angles involved in the embodiments of the present disclosure are all in degrees (indicated by the symbol °).

Figure 9A:
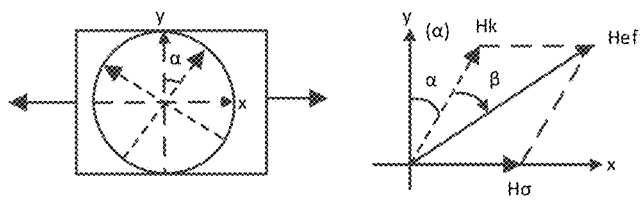
FIGS. 9A-9P are rotation angle diagrams of free layers of magnetoresistance sensor units under the action of tensile and compressive stresses at different initial magnetic moments.

FIGS. 9A-9P are magnetic moment rotation angle diagrams of the free layers of the magnetoresistance sensor units under the action of tensile and compressive stresses at different initial magnetic moment angles. The initial magnetic moment angles of the free layers specifically refer to the angles at which the initial magnetic moments of the free layers deviate from the Y-axis (specifically, +Y-axis), and the magnetic moments of the free layers are rotated after being subjected to the stresses. Here, the longitudinal direction of the deformable substrate is defined as the X-axis direction, the width direction of the deformable substrate is defined as the Y-axis direction, and the axial direction of the stress σ is the X-axis direction.

Figure 9B:
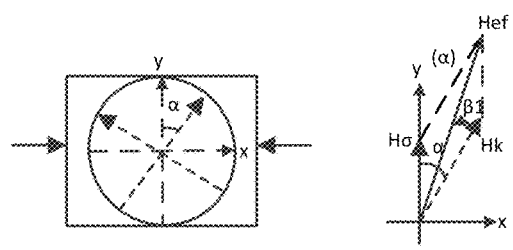
Figure 9C:
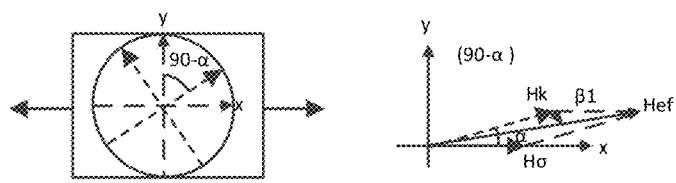
Figure 9D:
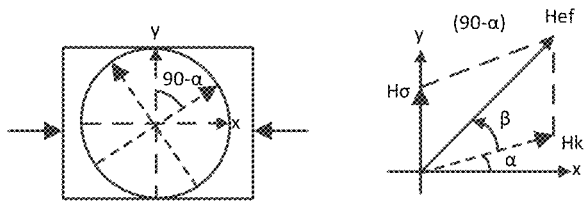
Figure 9E:
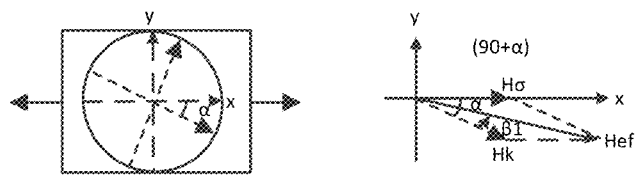
Figure 9F:
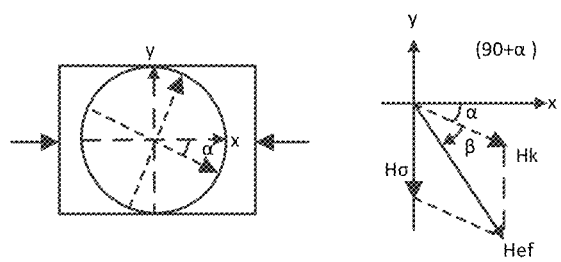
Figure 9G:
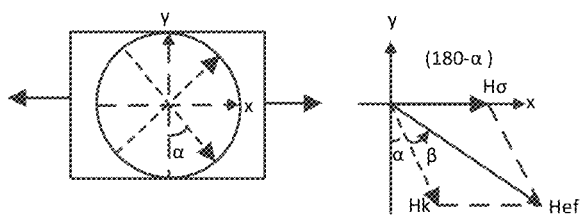
Figure 9H:
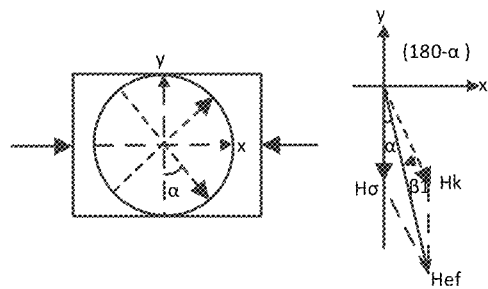
Figure 9I:
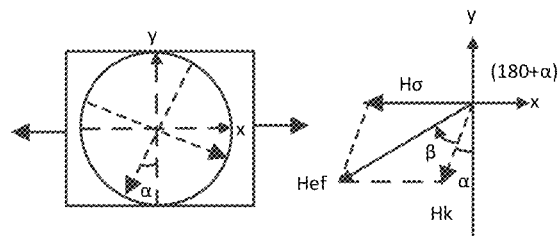
Figure 9J:
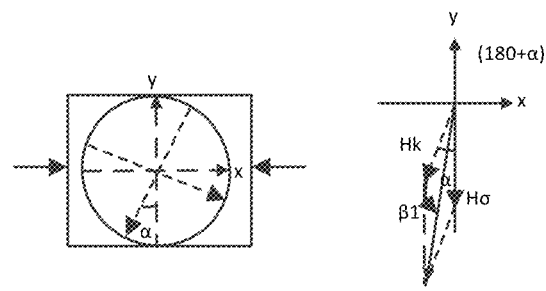
Figure 9K:
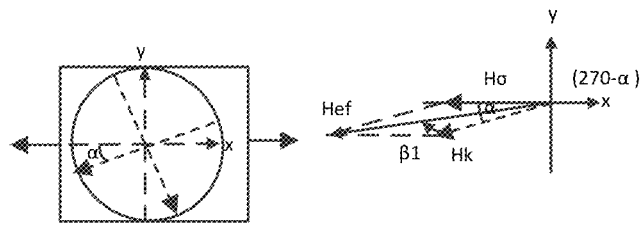
Figure 9L:
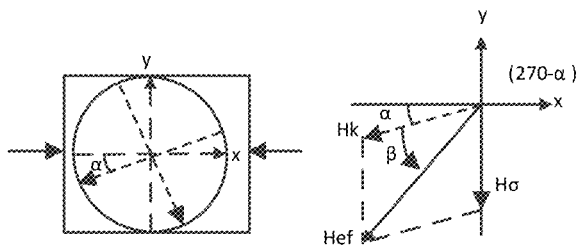
Figure 9M:
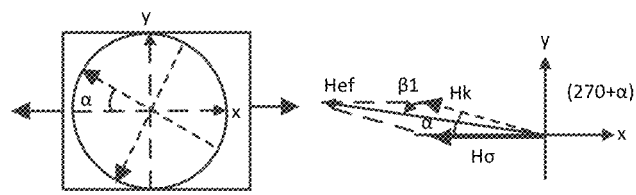

Referring to FIG. 9A, when the initial magnetic moments of the free layers deviate from the Y axis at an angle α, and the free layers bear a tensile stress σ greater than 0, the rotation angles of the magnetic moments of the free layers are β. Referring to FIG. 9B, when the initial magnetic moments of the free layers deviate from the Y axis at the angle α, and the free layers bear a compressive stress σ less than 0, the rotation angles of the magnetic moments of the free layers are β1. Referring to FIG. 9C, when the initial magnetic moments of the free layers deviate from the Y axis at an angle of 90−α, and the free layers bear a tensile stress σ greater than 0, the rotation angles of the magnetic moments of the free layers are β1. Referring to FIG. 9D, when the initial magnetic moments of the free layers deviate from the Y axis at the angle of 90−α, and the free layers bear a compressive stress σ less than 0, the rotation angles of the magnetic moments of the free layers are β. Referring to FIG. 9E, when the initial magnetic moments of the free layers deviate from the Y axis at an angle of 90+α, and the free layers bear a tensile stress σ greater than 0, the rotation angles of the magnetic moments of the free layers are β1. Referring to FIG. 9F, when the initial magnetic moments of the free layers deviate from the Y axis at the angle of 90+α, and the free layers bear a compressive stress σ less than 0, the rotation angles of the magnetic moments of the free layers are β. Referring to FIG. 9G, when the initial magnetic moments of the free layers deviate from the Y axis at an angle of 180−α, and the free layers bear a tensile stress σ greater than 0, the rotation angles of the magnetic moments of the free layers are β. Referring to FIG. 9H, when the initial magnetic moments of the free layers deviate from the Y axis at the angle of 180−α, and the free layers bear a compressive stress σ less than 0, the rotation angles of the magnetic moments of the free layers are β1. Referring to FIG. 9I, when the initial magnetic moments of the free layers deviate from the Y axis at an angle of 180+α, and the free layers bear a tensile stress σ greater than 0, the rotation angles of the magnetic moments of the free layers are β. Referring to FIG. 9J, when the initial magnetic moments of the free layers deviate from the Y axis at the angle of 180+α, and the free layers bear a compressive stress σ less than 0, the rotation angles of the magnetic moments of the free layers are β1. Referring to FIG. 9K, when the initial magnetic moments of the free layers deviate from the Y axis at an angle of 270−α, and the free layers bear a tensile stress σ greater than 0, the rotation angles of the magnetic moments of the free layers are β1. Referring to FIG. 9L, when the initial magnetic moments of the free layers deviate from the Y axis at the angle of 270−α, and the free layers bear a compressive stress σ less than 0, the rotation angles of the magnetic moments of the free layers are β. Referring to FIG. 9M, when the initial magnetic moments of the free layers deviate from the Y axis at an angle of 270+α, and the free layers bear a tensile stress σ greater than 0, the rotation angles of the magnetic moments of the free layers are β1. Referring to FIG. 9N, when the initial magnetic moments of the free layers deviate from the Y axis at the angle of 270+α, and the free layers bear a compressive stress σ less than 0, the rotation angles of the magnetic moments of the free layers are β. Referring to FIG. 9O, when the initial magnetic moments of the free layers deviate from the Y axis at an angle of 360−α, and the free layers bear a tensile stress σ greater than 0, the rotation angles of the magnetic moments of the free layers are β. Referring to FIG. 9P, when the initial magnetic moments of the free layers deviate from the Y axis at the angle of 360−α, and the free layers bear a compressive stress σ less than 0, the rotation angles of the magnetic moments of the free layers are β1. As described above, it can be seen that the magnetic moments of the free layers are rotated and their rotation angle values are respectively β and β1 after the tensile and compressive stresses are applied on the free layers. The calculation process of their rotation angle is as follows:

in a coordinate system, the tensile stress σ greater than 0 is equivalent to an equivalent magnetic field Hσ along the X-axis direction, and the compressive stress σ less than 0 is equivalent to another equivalent magnetic field Hσ along the Y-axis direction. When the magnetic moments Mf of the free layers and the Y-axis have different initial deflection angles, there is an anisotropic magnetic field Hk; and the magnetic moments of the free layers have an anisotropic magnetic field $H_{ef}$ after being rotated at a certain angle when not taking the effect of a demagnetizing field and other bias magnetic fields into account, where Hef is the vector sum of the magnetic fields Hk and Hσ, and Hef is the final magnetic moment orientation of the magnetic moments of the free layers. Taking the rotation angles β of the magnetic moments of the free layers and the initial magnetic moment deflection angles a of the free layers as shown in FIG. 9A as an example, the calculation is as follows:

$$X: H_\sigma + H_K * \sin\alpha = H_{ef} * \sin(\alpha + \beta) \quad (6)$$

$$Y: H_K * \cos\alpha = H_{ef} * \cos(\alpha + \beta)$$

$$\beta = \tan^{(-1)}\left(\frac{H_\sigma + H_K * \sin\alpha}{H_K * \cos\alpha}\right) - \alpha \quad (7)$$

Taking the rotation angles β1 of the magnetic moments of the free layers and the initial magnetic moment deflection angles a of the free layers as shown in FIG. 9B as an example, the calculation is as follows:

$$X: H_K * \sin\alpha = H_{ef} * \sin(\alpha - \beta_1) \quad (8)$$

$$Y: H_\sigma + H_K * \cos\alpha = H_{ef} * \cos(\alpha - \beta_1)$$

$$\beta_1 = \alpha - \tan^{(-1)}\frac{H_K * \sin\alpha}{H_\alpha + H_K * \cos\alpha} \quad (9)$$

Since the included angle Φ between the magnetic moment of the free layer and the magnetic moment of the pinning layer of each magnetoresistance sensor unit is 90° at the beginning, and the rotation angle of the magnetic moment of the free layer is ±β or ±β1, therefore: Φ=90°±β; Φ=90°±β; and obviously, β1 is not equal to β in general.

Referring to FIGS. 9A-9P, a relative relationship between the magnetic moments Mr of the pinning layers and the magnetic moments Mf of the free layers is as follows: the magnetic moments Mf of the free layers are rotated counterclockwise by 90° to obtain the magnetic moments Mr of the pinning layers, so that the magnetic moments, obtained by rotating the magnetic moments of the free layers counterclockwise, of the pinning layers are defined as CCW (counterclockwise); and on the contrary, the magnetic moments Mf of the free layers is rotated clockwise by 90° to obtain the magnetic moments Mr of the pinning layers, so that the magnetic moments, obtained by rotating the magnetic moments of the free layers clockwise, of the pinning layers are defined as CW (clockwise).

Table 1 lists the rotational magnetic moments of the free layers under tensile stresses and compressive stresses when the magnetic moments of the free layers are at different initial deflection angles, where + represents an increase in the included angle between the free layers and the pinning layers, and − represents a decrease in the included angle between the free layers and the pinning layers. It can be seen from Table 1 that the rotation angle amplitudes of the free layers with the same initial deflection angle are different under the conditions that the tensile stresses σ greater than 0 and the compressive stresses σ less than 0, which are β1 and β, or β and β1, respectively. In addition, the rotation directions of the free layers with the same initial deflection angle are also different, which are +and −, or − and +, respectively. Table 1 is as follows:

| Angle | σ > 0 | σ < 0 |
|---|---|---|
| α | +β | −β1 |
| 90 − α | +β1 | −β |
| 90 + α | −β1 | +β |
| 180 − α | −β | +β1 |
| 180 + α | +β | −β1 |
| 270 − α | +β1 | −β |
| 270 + α | −β1 | +β |
| 360 − α | −β | +β1 |

FIGS. 10A-10D are circumferential distribution diagrams of initial magnetic moment angles and rotation angles of the free layers under the action of the tensile stress and the compressive stress, where β denotes a solid circle, +β denotes + existing in the solid circle, and −βdenotes − existing in the solid circle; and β1 denotes a hollow circle, +β1 denotes+existing in the hollow circle, and −β1 denotes − existing in the hollow circle. xxx no means that the angular position is invalid, the inner circle represents the tensile stress (σ>0), the outer circle represents the compressive stress (σ<0), and the arrows represent the initial magnetic moment angle orientation of the magnetic moments Mf of the free layers on the cantilever beams.

FIG. 10A shows the inner ring TMR/outer ring TMR=CCWσ>0/CCWσ<0 represented in FIGS. 9A-9P; FIG. 10B shows the inner ring TMR/outer ring TMR=CWσ>0/CWσ<0 represented in FIGS. 9A-9P; FIG. 10C shows the inner ring TMR/outer ring TMR=CCWσ>0/CWσ<0 represented in FIGS. 9A-9P; and FIG. 10D shows the inner ring TMR/outer ring TMR=CWσ>0/CCWσ<0 represented in FIGS. 9A-9P.

According to the structure of the hydrogen gas sensor shown in FIG. 6, the push magnetoresistance sensor units and the pull magnetoresistance sensor units bear stresses of the same magnitude and in the opposite directions under the action of the tensile stress σ greater than 0 and the compressive stress σ less than 0, then the change values of the included angles between the free layers and the pinning layers of each push magnetoresistance sensor unit and each pull magnetoresistance sensor unit have the characteristics of being equal in magnitudes and opposite in directions. That is to say, the rotation angles of the free layers of the push magnetoresistance sensor units are required to be +β when the tensile stress σ is greater than 0, and the rotation angles of the free layers of the pull magnetoresistance sensor units are required to be −β when the compressive stress σ is less than 0; or, the rotation angles of the free layers of the push magnetoresistance sensor units are required to be +β1 when the tensile stress a is greater than 0, and the rotation angles of the free layers of the pull magnetoresistance sensor units are required to be −β1 when the compressive stress σ is less than 0. In combination with the circumferential distribution diagrams of FIGS. 10A-10D, it is required to respectively find the symbols corresponding to +β and −β or the symbols corresponding to +β1 and −β1 in the inner ring and the outer ring.

The push-pull bridge structure shown in FIG. 6 corresponds to the CCW/CCW and CW/CW structures, that is, the magnetic moments of the free layers of the push magnetoresistance sensor units and the magnetic moments of the free layers of the pull magnetoresistance sensor units are simultaneously rotated clockwise or counterclockwise by the same angle to obtain the corresponding magnetic moments of the pinning layers, and the corresponding initial magnetic moment angle relationship of a push arm and a pull arm is shown below.

Referring to FIG. 10A, the rotation angles of the free layers of the push magnetoresistance sensor units are +β when the tensile stress σ is greater than 0, then their inner circle should be checked, and the angles corresponding to +β include α and 180+α; and at this time, it is required that the rotation angles of the free layers of the pull magnetoresistance sensor units should be −β when the compressive stress σ is less than 0, then their outer ring should be checked, and the angles corresponding to −β include 90-α and 270-α. Referring to FIG. 10B, the rotation angles of the free layers of the push magnetoresistance sensor units are +β when the tensile stress σ is greater than 0, then their inner circle should be checked, and the angles corresponding to +β include 360-α and 180-α; and at this time, it is required that the rotation angles of the free layers of the pull magnetoresistance sensor units should be −β when the compressive stress a is less than 0, then their outer ring should be checked, and the angles corresponding to −β include 90+α and 270+α.

Referring to FIG. 10A, the rotation angles of the free layers of the push magnetoresistance sensor units are +β1 when the tensile stress a is greater than 0, then their inner circle should be checked, and the angles corresponding to +β1 include 90-α and 270-α; and at this time, it is required that the rotation angles of the free layers of the pull magnetoresistance sensor units should be −β1 when the compressive stress σ is less than 0, then their outer ring should be checked, and the angles corresponding to −β1 include a and 180+α. Referring to FIG. 10B, the rotation angles of the free layers of the push magnetoresistance sensor units are +β1 when the tensile stress a is greater than 0, then their inner circle should be checked, and the angles corresponding to +β1 include 90+α and 270+α; and at this time, it is required that the rotation angles of the free layers of the pull magnetoresistance sensor units should be −β1 when the compressive stress a is less than 0, then their outer ring should be checked, and the angles corresponding to −β1 include 360-α and 180-α.

The relationships between the initial magnetic moment angles of push arms and the initial magnetic moment angles of pull arms are shown in Table 2, where the push arms and the pull arms separately correspond to the push-pull magnetoresistive bridge stress sensor structure having a CCW/CCW structure and the push-pull magnetoresistive bridge stress sensor structure having a CW/CW structure. For two configurations of TMR being CCWσ>0/CCWσ<0 and CWσ>0/CWσ<0, when the rotation angles of the free layers are +β and −β, or +β1 and −β1, the initial magnetic moment angles 90-α and 270-α of the pull arms correspond to any one of the initial magnetic moment angles α of the push arms. Table 2 is as follows:

| Deflection angle | Push arm (σ > 0) | Pull arm (σ < 0) | Deflection angle | Push arm (σ > 0) | Pull arm (σ < 0) |
|---|---|---|---|---|---|
| β | α | 90 − α | β1 | 90 − α | α |
|   |   | 270 − α |   |   | 180 + α |
|   | 180 − α | 90 + α |   | 90 + α | 180 − α |
|   |   | 270 + α |   |   | 360 − α |
|   | 180 + α | 270 − α |   | 270 − α | 180 + α |
|   |   | 90 − α |   |   | α |
|   | 360 − α | 270 + α |   | 270 + α | 360 − α |
|   |   | 90 + α |   |   | 180 − α |

Similarly, the push-pull bridge structure shown in FIG. 6 corresponds to the CCW/CW and CW/CCW structures, that is, the magnetic moments of the free layers of the push magnetoresistance sensor units and the magnetic moments of the free layers of the pull magnetoresistance sensor units are rotated by the same angle and in different directions to obtain the corresponding magnetic moments of the pinning layers, and the relationships between the initial magnetic moment angles of the corresponding push arms and the corresponding pull arms refer to FIG. 10C and FIG. 10D, so that the contents of Table 3 are obtained. For two configurations of TMR being CCWσ>0/CWσ<0 and CWσ>0/CCWσ<0, when the rotation angles of the free layers are +β and −β, or +β1 and −β1, the initial magnetic moment angles 90+α and 270+α of the pull arms correspond to any one of the initial magnetic moment angles α of the push arms. Table 3 is as follows:

| Deflection angle | Push arm (σ > 0) | Pull arm (σ < 0) | Deflection angle | Push arm (σ > 0) | Pull arm (σ < 0) |
|---|---|---|---|---|---|
| β | α | 90 + α | β1 | 90 − α | 360 − α |
|   |   | 270 + α |   |   | 180 − α |
|   | 180 − α | 90 − α |   | 90 + α | 180 + α |
|   |   | 270 − α |   |   | α |
|   | 180 + α | 270 + α |   | 270 − α | 180 − α |
|   |   | 90 + α |   |   | 360 − α |
|   | 360 − α | 270 − α |   | 270 + α | α |
|   |   | 90 − α |   |   | 180 + α |

In one exemplary embodiment, on the basis of the above technical solution, optionally, the deformable substrate has a first surface and a second surface which are arranged along the Z-axis direction; the magnetoresistive bridge stress sensor has the push-pull bridge structure, and includes the push magnetoresistance sensor units and the pull magnetoresistance sensor units; the push magnetoresistance sensor units and the pull magnetoresistance sensor units are disposed on the first surface or on the second surface at the same time, and the push magnetoresistance sensor units and the pull magnetoresistance sensor units bear stresses of the same magnitude and in the same direction. Optionally, the deformable substrate is the cantilever beam or the membrane assembly, its first surface and second surface are both parallel to the plane X-Y, and its Z-axis direction is perpendicular to the plane X-Y, where the push magnetoresistance sensor units and the pull magnetoresistance sensor units are located on the same surface of the deformable substrate, for example, the push magnetoresistance sensor units and the pull magnetoresistance sensor units are both located on the lower surface of the deformable substrate, or on the upper surface of the deformable substrate at the same time.

Figure 11:
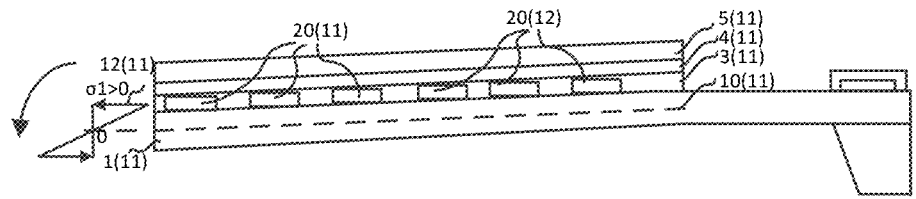
FIG. 11 is a schematic diagram of the push-pull magnetoresistive bridge stress sensor as well as its structure and stress distribution on the cantilever beam provided by the embodiments of the present disclosure.

FIG. 11 shows the push-pull magnetoresistive bridge stress sensor as well as its structure and stress distribution diagram on the cantilever beam. Both the push magnetoresistance sensor units 20 (11) and the pull magnetoresistance sensor units 20 (12) are located on the upper surface of the cantilever beam 1 (11), and are isolated by covering on their surfaces with the electrical isolation layer 3 (11); the magnetic shielding layer 4 (11) is located above the push magnetoresistance sensor units 20 (11) and the pull magnetoresistance sensor units 20 (12) for shielding the influence of external magnetic fields; and the hydrogen sensing layer 5 (11) is located at the top so as to directly react with hydrogen gas, and the plane 10 (11) is the zero-strain plane of the cantilever beam 1 (11). The deformation of the hydrogen sensing layer 5 (11) will cause the cantilever beam 1 (11) to bend downward, and a tensile stress σ greater than 0 12 (11) will be generated in both the push magnetoresistance sensor units 20 (11) and the pull magnetoresistance sensor units 20 (12).

Figure 12:
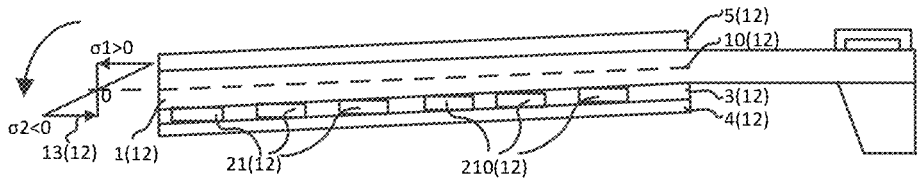
FIG. 12 is a schematic diagram of the push-pull magnetoresistive bridge stress sensor as well as its structure and stress distribution on the cantilever beam provided by the embodiments of the present disclosure.

FIG. 12 shows the push-pull magnetoresistive bridge stress sensor as well as its structure and stress distribution diagram on the cantilever beam. Both the push magnetoresistance sensor units 21 (12) and the pull magnetoresistance sensor units 210 (12) are located on the upper surface of the cantilever beam 1 (12), and are isolated by covering on their surfaces with the electrical isolation layer 3 (12); the magnetic shielding layer 4 (12) is located above the push magnetoresistance sensor units 21 (12) and the pull magnetoresistance sensor units 210 (12) for shielding the influence of external magnetic fields; and the hydrogen sensing layer 5 (12) is located on the upper surface of the cantilever beam 1 (12) so as to directly react with hydrogen gas, and the plane 10 (11) is the zero-strain plane of the cantilever beam. The cantilever beam will bend downward, and a compressive stress σ13 (12), which is less than 0, will be generated in both the push magnetoresistance sensor units 20 (11) and the pull magnetoresistance sensor units 20 (12).

Figure 13:
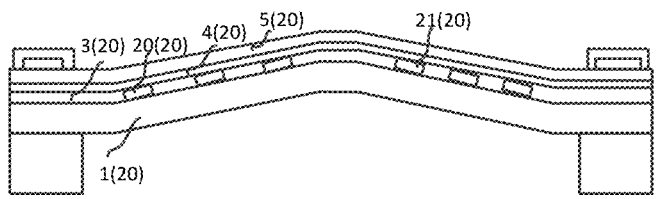
FIG. 13 is a schematic diagram of the push-pull magnetoresistive bridge stress sensor as well as its structure and stress distribution on the membrane assembly provided by the embodiments of the present disclosure.

FIG. 13 shows the push-pull magnetoresistive bridge stress sensor as well as its structure and stress distribution diagram on the membrane. The structure includes a diagram 1 (20), the push magnetoresistance sensor units 20 (20) and the pull magnetoresistance sensor units 21 (20) which are located on the diagram 1 (20), the electrical isolation layer 3(20), the magnetic shielding layer 4 (20) located above the push magnetoresistance sensor units 20 (20) and the pull magnetoresistance sensor units 21 (20), and the hydrogen sensing layer 5 (20) located at the top; and at this point, the hydrogen sensing layer 5 (20) expands or elongates in volume after absorbing hydrogen gas, and the membrane will bend upward accordingly.

Figure 14:
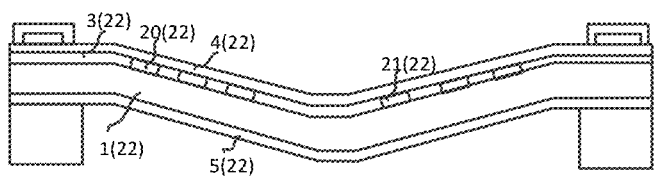
FIG. 14 is a schematic diagram of the push-pull magnetoresistive bridge stress sensor as well as its structure and stress distribution on the membrane assembly provided by the embodiments of the present disclosure.

FIG. 14 shows the push-pull magnetoresistive bridge stress sensor as well as its structure and stress distribution diagram on the membrane. The structure includes a diagram 1 (22), the push magnetoresistance sensor units 20 (22) and the pull magnetoresistance sensor units 21 (22) which are located on the diagram 1 (22), the electrical isolation layer 3 (22), the magnetic shielding layer 4 (22) located above the push magnetoresistance sensor units 20 (22) and the pull magnetoresistance sensor units 21 (22), and the hydrogen sensing layer 5 (22) located at the bottom; and at this point, the hydrogen sensing layer 5 (22) expands or elongates in volume after absorbing hydrogen gas, and the membrane will bend downward accordingly.

Optionally, the angle at which the initial magnetic moment of the free layer of each push magnetoresistance sensor unit deviates from the Y-axis is a; when the magnetic moments of the free layers of the push magnetoresistance sensor units and the magnetic moments of the free layers of the pull magnetoresistance sensor units are simultaneously rotated clockwise or counterclockwise by 90° to obtain the corresponding magnetic moments of the pinning layers, the angle at which the initial magnetic moment of the free layer of each pull magnetoresistance sensor unit deviates from the Y-axis is 180-α or 360-α; or, when the magnetic moments of the free layers of the push magnetoresistance sensor units and the magnetic moments of the free layers of the pull magnetoresistance sensor units are rotated in different directions and by the same angle, the angle at which the initial magnetic moment of the free layer of each pull magnetoresistance sensor unit deviates from the Y-axis is a or 180+α; and the value range of α is from 0° to 360°, where when the free layers are made of a material with a positive magnetostriction coefficient and bear a tensile stress or made of a material with a negative magnetostriction coefficient and bear a compressive stress, α is not 0° or 180°, and when the free layers are made of a material with a positive magnetostriction coefficient and bear a compressive stress or made of a material with a negative magnetostriction coefficient and bear a tensile stress, α is not 90° or 270°.

Figure 15A:
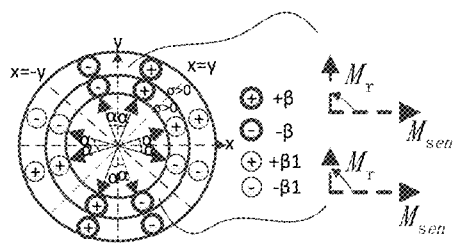
Figure 15B:
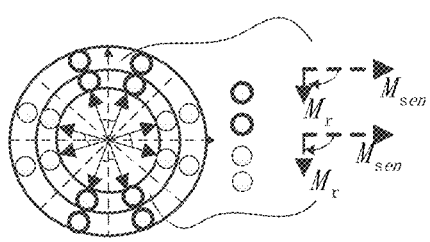
Figure 15C:
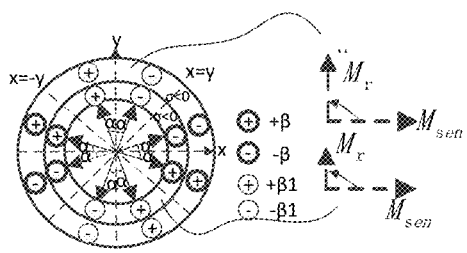
Figure 15D:
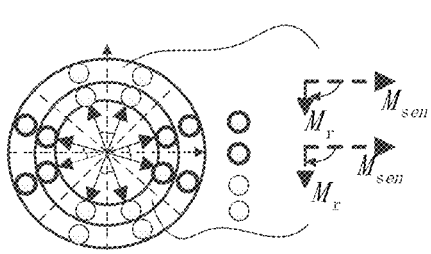

FIGS. 15A-15F are circumferential distribution diagrams of the initial magnetic moment angles and the rotation angles of the free layers of the hydrogen gas sensor, shown in FIGS. 11-14, under the action of the tensile stress and the compressive stress. FIG. 15A is a configuration of CCWσ>0/CCWσ>0, FIG. 15B is a configuration of CWσ>0/CWσ>0, FIG. 15C is a configuration of CCWσ<0/CCWσ<0, and FIG. 15D is a configuration of CWσ<0/CWσ<0, where, the magnetic moments of the free layers of the push magnetoresistance sensor units and the magnetic moments of the free layers of the pull magnetoresistance sensor units are simultaneously rotated clockwise or counterclockwise by 90° to obtain the corresponding magnetic moments of the pinning layers. FIG. 15E is a configuration of CWσ>0/CCWσ>0, and FIG. 15F is a configuration of CCWσ<0/CWσ<0, where the magnetic moments of the free layers of the push magnetoresistance sensor units and the magnetic moments of the free layers of the pull magnetoresistance sensor units are rotated by the same angle and in different directions. The analysis method of the circumferential distribution process is similar to that of FIGS. 9A-9P, and will not be repeated here.

Table 4 shows relationships between the initial magnetic moment angles of the push arms and the pull arms which separately correspond to the push-pull magnetoresistive bridge stress sensors having four configurations of CCWσ>0/CCWσ>0, CWσ>0/CWσ>0, CCWσ<0/CCWσ<0, CWσ<0/CWσ<0; and when the rotation angles of the free layers are +β and −β, or +β1 and −β1, the initial magnetic moment angles 180-α and 360-α of the pull arms correspond to any one of the initial magnetic moment angles α of the push arms. Table 4 is as follows:

| Deflection angle | Push arm (σ > 0) | Pull arm (σ > 0) | Deflection angle | Push arm (σ > 0) | Pull arm (σ < 0) |
|---|---|---|---|---|---|
| β | α | 180 − α | β1 | 90 − α | 90 + α |
|   |   | 360 − α |    |        | 270 + α |
|   | 180 − α | α |    | 90 + α | 90 − α |
|   |         | 180 + α |  |      | 270 − α |
|   | 180 + α | 180 − α |  | 270 − α | 270 + α |
|   |         | 360 − α |  |         | 90 + α |
|   | 360 − α | α |      | 270 + α | 270 − α |
|   |         | 180 + α |  |        | 90 − α |

Table 5 shows relationships between the initial magnetic moment angles of the push arms and the pull arms which separately correspond to the structures II of the push-pull magnetoresistive bridge stress sensors having two configurations of CWσ>0/CCWσ>0 and CCWσ<0/CWσ<0; and when the rotation angles of the free layers are +β and −β, or +β1 and −β1, the initial magnetic moment angles α and 180+α of the pull arms correspond to any one of the initial magnetic moment angles α of the push arms. Table 5 is as follows:

| Deflection angle | Push arm (σ > 0) | Pull arm (σ > 0) | Deflection angle | Push arm (σ > 0) | Pull arm (σ > 0) |
|---|---|---|---|---|---|
| β | α | α | β1 | 90 − α | 90 − α |
|   |   | 180 + α |  |       | 270 − α |
|   | 180 − α | 180 − α |  | 90 + α | 90 + α |
|   |         | 360 − α |  |        | 270 + α |
|   | 180 + α | 180 + α |  | 270 − α | 270 − α |
|   |         | α       |  |         | 90 − α |
|   | 360 − α | 360 − α |  | 270 + α | 270 + α |
|   |         | 180 − α |  |         | 90 + α |

It should be noted that, in the above diagrammatic presentation, the initial magnetic moment angles α of the free layers of the push magnetoresistance sensor units may be any angle in a range of 0-360°; while if the initial magnetic moment angles of the free layers of the pull magnetoresistance sensor units exceeds 360°, the their values can be returned to the range of 0-360° by subtracting a period of 360°; and in addition, for a tensile stress a greater than 0, α is not equal to 90° and 270°, and for a compressive stress a less than 0, α is not equal to 0° and 180°.

In one exemplary embodiment, on the basis of the above technical solution, optionally, the hydrogen gas sensor further includes: a non-hydrogen sensing layer in the same layer as the hydrogen sensing layer; the deformable substrate includes the cantilever beam or the membrane assembly; the cantilever beam includes a fixed part and a reference cantilever beam and a sensing cantilever beam which are respectively disposed at the two sides of the fixed part, the reference cantilever beam is provided with a reference area, and the sensing cantilever beam is provided with a sensing area; or, the membrane assembly includes a reference membrane and a sensing membrane which are enclosed in the frame, the reference membrane is provided with a reference area, and the sensing membrane is provided with a sensing area; and the hydrogen sensing layer is disposed on the magnetic shielding layer within the sensing area, and the non-hydrogen sensing layer is disposed on the magnetic shielding layer within the reference area. Here, the magnetoresistive bridge stress sensor is disposed on the same side surface of the deformable substrate, for example, disposed on the upper surface, and can also be optionally disposed on the lower surface in other embodiments.

Optionally, the reference area and the sensing area of the deformable substrate are located on the same plane; the magnetoresistive bridge stress sensor has a reference bridge structure, and includes reference magnetoresistance sensor units and sensing magnetoresistance sensor units; and the reference magnetoresistance sensor units are disposed in the reference area, and the sensing magnetoresistance sensor units are disposed in the sensing area. Here, the reference magnetoresistance sensor units and the sensing magnetoresistance sensor units are disposed on the same side surface of the deformable substrate, for example, both disposed on the upper surface or the lower surface.

FIG. 16 shows the reference bridge type magnetoresistive bridge stress sensor as well as its structure and stress distribution diagram on the cantilever beam. The deformable substrate includes the two cantilever beams, which are respectively the sensing cantilever beam 1 (14) and the reference cantilever beam 1 (15). The sensing magnetoresistance sensor units 30 (14) are located on the surface of the reference cantilever beam 1 (14), and the reference magnetoresistance sensor units 30 (15) are located on the surface of the reference cantilever beam 1 (15); the electrical isolation layers 3 (14) and 3 (15) are respectively located on the surfaces of the sensing magnetoresistance sensor units 30 (14) and the reference magnetoresistance sensor units 30 (15); and in addition, the hydrogen sensing layer 5 (14) and the non-hydrogen sensing layer 5' (15) are located on the top layers of the sensing cantilever beam 1 (14) and the reference cantilever beam 1 (15), respectively. When the hydrogen sensing layer 5(14) encounters hydrogen gas, it will undergo dimensional changes and generate a stress σ1, but the non-hydrogen sensing layer 5' (15) will not change; and therefore, the hydrogen sensing layer and the non-hydrogen sensing layer form a sensing bridge arm and a reference bridge arm of the reference bridge type magnetoresistive bridge stress sensor.

FIG. 17 shows the reference bridge type magnetoresistive bridge stress sensor as well as its structure and stress distribution diagram on the membrane assembly. The deformable substrate includes: the sensing membrane 62 (1) and the reference membrane 62 (2), where all sides of the sensing membrane 62 (1) are located on the substrate frame 61 (1), and all sides of the reference membrane 62 (2) are located on the substrate frame 61 (2); the sensing magnetoresistance sensor units 63 (1) are located on the sensing membrane 62 (1), the reference magnetoresistance sensor units 63 (2) are located on the reference membrane 62 (2), and the sensing magnetoresistance sensor units 63 (1) and the reference magnetoresistance sensor units 63 (2) are electrically connected to form the reference bridge type tunneling magnetoresistive bridge stress sensor.

FIG. 18 shows a side view of the reference bridge type magnetoresistive bridge stress sensor and its structure on the membrane assembly. The structure includes the reference membrane 1 (17), the sensing membrane 1 (16), the reference magnetoresistance sensor units 20 (16) located on the reference membrane 1 (17), the sensing magnetoresistance sensor units 20 (17) located on the sensing membrane 1 (16), the electrical isolation layer 3 (16) covered between the reference magnetoresistance sensor units 20 (16), the electrical isolation layer 3 (17) covered between the sensing magnetoresistance sensor units 20 (17), the magnetic shielding layers 4 (16) and 4 (17) located above the magnetoresistance sensor units 20 (16) and 20 (17), and the uppermost hydrogen sensing layer 5 (16) and non-hydrogen sensing layer 5 (17), where the reference membrane 1 (16) and the sensing membrane 1 (17), the magnetic shielding layers 4

(16) and 4 (17) as well as the electrical isolation layer 3 (16) and 3 (17) are continuous materials at the same layer, while the hydrogen sensing layer 5 (16) and the non-hydrogen sensing layer 5 (17) are at the same layer, but discontinuous materials.

When the hydrogen gas sensor is exposed to the air, the hydrogen sensing layer 5 (16) absorbs hydrogen gas and expands, but is constrained by the sensing membrane 1 (16), so that the membrane bends, and the sensing magnetoresistance sensor units 20 (16) experience the compressive stress at this time; when the hydrogen sensing layer is located above the membrane, the membrane bends downward, and the sensing magnetoresistance sensor units 20 (17) experience the tensile stress; and when the hydrogen sensing layer is located under the membrane, the membrane bends upward, but the non-hydrogen sensing layer 5 (17) is not affected by hydrogen gas, does not bend, and experiences an intrinsic stress.

Optionally, the angle at which the initial magnetic moment of the free layer of each reference magnetoresistance sensor unit deviates from the Y-axis is $\alpha$, and the angle at which the initial magnetic moment of the free layer of each sensing magnetoresistance sensor unit deviates from the Y-axis is $\alpha$; the magnetic moments of the free layers of the reference magnetoresistance sensor units and the magnetic moments of the free layers of the sensing magnetoresistance sensor units are simultaneously rotated clockwise or counterclockwise by the same angle to obtain the corresponding magnetic moments of the pinning layers; and the value range of $\alpha$ is from 0° to 360°, where when the free layers are made of a material with a positive magnetostriction coefficient and bear a tensile stress or made of a material with a negative magnetostriction coefficient and bear a compressive stress, $\alpha$ is not 0° or 180°, and when the free layers are made of a material with a positive magnetostriction coefficient and bear a compressive stress or made of a material with a negative magnetostriction coefficient and bear a tensile stress, $\alpha$ is not 90° or 270°.

FIGS. 19A-19D are circumferential distribution diagrams of the initial magnetic moment angles and the rotation angles of the free layers under the action of reference tensile and compressive stresses. Since the tunnel magnetoresistance sensor units may also bring additional stresses, the residual stress in the layer of the reference magnetoresistance sensor units 30 (15) is approximately 0, that is, $\sigma$ is approximately equal to 0. It is necessary for the reference magnetoresistance sensor units 30 (15) to choose the same position and magnetic moment orientation relationship as the sensing magnetoresistance sensor units 30 (14), so that the influence of the residual stress can be eliminated as much as possible. Based on this, the angular orientation of the initial magnetic moments of the free layers of the sensing magnetoresistance sensor units or the reference magnetoresistance sensor units is as follows:

FIG. 19A shows the circumferential distribution under the condition of CCW$\sigma$>0/CCW$\sigma$≈0, FIG. 19B shows the circumferential distribution under the condition of CCW$\sigma$<0/CCW$\sigma$≈0, FIG. 19C shows the circumferential distribution under the condition of CW$\sigma$>0/CW$\sigma$≈0, and FIG. 19D shows the circumferential distribution under the condition of CW$\sigma$<0/CW$\sigma$≈0, so the orientation of the free layers of the sensing magnetoresistance sensor units or the reference magnetoresistance sensor units can be: in the case of the tensile stress $\sigma$ being greater than 0, the initial magnetic moment angles $\alpha$ of their free layers are not equal to 0° and 180°, and in the case of the compressive stress $\sigma$ being less than 0, the initial magnetic moment angles $\alpha$ of their free layers are not equal to 90° and 270°.

The structures of the push-pull magnetoresistive bridge stress sensors described in the above embodiments are shown in FIGS. 20A-20B. FIG. 20A shows the push-pull magnetoresistive bridge stress sensor having a half-bridge structure, and FIG. 20B shows the push-pull magnetoresistive bridge stress sensor having a full-bridge structure. The push magnetoresistance sensor units 20 and the pull magnetoresistance sensor units 21 respectively form the push arms and the pull arms of the magnetoresistive bridge stress sensors.

The structures of the reference magnetoresistive bridge stress sensors described in the above embodiments are shown in FIGS. 20C-20D. FIG. 20C shows the reference magnetoresistive bridge stress sensor having a half-bridge structure, and FIG. 20D shows the reference magnetoresistive bridge stress sensor having a full-bridge structure. The sensing magnetoresistance sensor units 30 (14) and the reference magnetoresistance sensor units 30 (15) respectively form the sending arms and the reference arms of the magnetoresistive bridge stress sensors.

For the magnetoresistive bridge stress sensor, optionally, the magnetic shielding layer is a soft magnetic shielding layer, and is made of a soft magnetic alloy material containing Co, Fe and Ni. Optionally, the electrical isolation layer is made from photoresist, $Al_2O_3$, SiN, $SiO_2$ or SiC. Optionally, the hydrogen sensing layer is made from $AB_5$, $AB_3$, $AB_2$, AB, and $A_2B$ type intermetallic compounds, where A represents a strong metal hydride forming element such as rare earth metals, Ca, Mg, Zr or Ti, and B represents a transition metal including Ni, Co, Fe, Mn and Cr.

$AB_5$ alloys include $LaNi_5$ and $RNi_5$, where R is rare earth metal; $MmNi_5$ and Mm are rare earth mixtures, containing 48-50% of Ce, 32-34% of La, 13-14% of Nd, 4-5% of Pr, and 1.5% of other rare earth elements; La-rich Mm is called Lm or Ml, and the typical Lm contains 48% of La, 25% of Ce, 6% of Pr, 21% of Nd and 0.3% of other rare earth elements; $CaNi5$; and substitutional $AB_5$ multi-element alloy, where A and B in $AB_5$ are locally replaced by other metals, rare earth metals in A are replaced by each other, for example, $CeNi_5$, $PrNi_5$ and $NdNi_5$ are replaced by $LaNi_5$, the rare earth metals and Ca are replaced by each other, for example, $Mm_{1-x}Ca_xNi_5$ and Mm can be partially replaced by Ti, Zr, B and Cu, and Ni atoms in $ANi5$ are partially replaced by other elements such as Co, Mn, Al, Cr, Fe, Cu, Tin, Si and B.

The $AB_2$ type intermetallic compound alloys include: binary $AB_2$ alloys, such as Zr-based $AB_2$laves alloy ZrM2 (M=V, Cr, Mn, Fe, Co, Mo); ternary and multicomponent $AB_2$ alloys, such as $Zr(FexCr_{1-x})_2$, $Zr(Fe_{0.75}Cr_{0.25})_2$, $Zr(Fe_xMn_{1-x})_2$ (x=0-0.8), $Ti_{0.98}Zr_{0.02}V_{0.43}Fe_{0.09}Cr_{0.05}Mn_{1.5}$, $Ti_{0.9}Zr_{0.1}Mn_{1.4}V_{0.2}Cr_{0.4}$, $Ti_{1+x}Cr_{2-y}Mn_y$(x=0.1-0.3, y=0-1.0), and $Ti_xCr_{2-y}V_y$(x=1.1-1.3, y=0.5-1.0), Cr, V or Mn being partially replaced with other elements such as Fe, Co, Ni, Al or Cu.

AB alloys include: TiFe, TiCo, and ZrNi; and substitutional AB alloys, where TiFe is partially replaced by transition elements such as Mn, Cr, V, Co, Ni, Mo and Cu, $TiFe_{1-x}Mn_x$(x=0.1-0.3), $TiFe_{0.8}Mn_yA_z$ (A=Zr, Al), $TiFe_{1-x}Ni_yA_z$ (A=Al, Co, Cr, La, Mn, Mo, Nb, V, Zr).

The hydrogen sensing layer also include Mg-based alloys such as $Mg_2Ni$, $Mg_2Cu$ and $La_2Mg_{17}$, Mg-rare earth alloys including $LnMg_{12}$(Ln=La, Ce, Mm), $Ln_2Mg_{17}$(Ln=La, Ce) and $Ln_5Mg_{41}$(Ln=Ce), other binary Mg alloys including $Mg_{17}Ba$, $Mg_3Cd$, $Mg_3Sb_2$, MgSn, MgZn, $Mg_2Pb$, $Mg_2Ca$, Mg$_2$Sn, Mg$_2$Si and MgLi, and substitutional Mg-based alloys including Mg$_2$Ni, Mg$_2$Cu, Mg$_2$Ni$_{0.75}$M$_{0.25}$(M=V, Cr, Fe, Co, Zn).

The hydrogen sensing layer further includes V and V-based alloys: V—Ti—M (M=Fe, Cr, Mn, Ge), such as (V$_{0.9}$Ti$_{0.1}$)$_{1-x}$Fe$_x$(x=0-0.075), Ti—V -Mn, Ti—V—Cr, V—Ti—Ni.

It should be pointed out that the free layers of the above mentioned TMR stress sensing elements have the positive magnetostriction coefficients λs greater than 0, including: CoFeB, CoFe and NiFe high magnetostriction materials. In fact, the free layers can also have the negative magnetostriction coefficients λs less than 0. The difference is only that λs less than 0 and σ greater than 0 are equivalent to λs greater than 0 and σ less than 0; less than 0 and σ less than 0 are equivalent to λs greater than 0 and σ greater than 0. It has no effect on the in-phase CCW/CCW and CW/CW or out-of-phase CCW/CW and CW/CCW of the push-pull magnetoresistive bridge stress sensor as well as in-phase CCW/CCW and CW/CW of the reference magnetoresistive bridge stress sensor being the initial phase relationship between the magnetoresistance sensor units. The difference is that when λs is greater than 0, the initial angles of the magnetoresistance sensor units under the tensile stress σ greater than 0 is not 0° or 180°, and the initial angles of the magnetoresistance sensor units under the compressive stress σ less than 0 is not 90° or 270°.

It should be noted that the above are only exemplary embodiments of the present disclosure and technical principles applied thereby. Those skilled in the art will understand that the present disclosure is not limited to the specific embodiments described herein, and various obvious changes, readjustments, combinations and substitutions can be made by those skilled in the art without departing from the protection scope of the present disclosure. Therefore, although the present disclosure has been described in detail through the above embodiments, the present disclosure is not limited to the above embodiments, and can also include other equivalent embodiments without departing from the concept of the present disclosure. The scope of this disclosure is determined by the scope of the attached claims.

The invention claimed is:

1. A hydrogen gas sensor utilizing electrically isolated tunneling magnetoresistive stress sensing elements, comprising:
   a deformable substrate;
   a magnetoresistive bridge stress sensor located on the deformable substrate, an electrical isolation layer covering the magnetoresistive bridge stress sensor, and a magnetic shielding layer located on the electrical isolation layer; and
   a hydrogen sensing layer located above the deformable substrate, where in the hydrogen sensing layer is located in a plane perpendicular to the deformation of the substrate covering the electrical isolation layer, the hydrogen sensing layer is configured to absorb or desorb hydrogen gas to generate expansion or contraction deformation and thus cause a stress change of the deformable substrate, and the magnetoresistive bridge stress sensor is configured to measure a hydrogen gas concentration utilizing the stress change of the deformable substrate.

2. The hydrogen gas sensor according to claim 1, wherein the deformable substrate is a cantilever beam; or,
   the deformable substrate is a membrane assembly; and the membrane assembly comprises a frame and a membrane enclosed in the frame, and the magnetoresistive bridge stress sensor is disposed on the membrane.

3. The hydrogen gas sensor according to claim 2, wherein the length direction of the deformable substrate is the X-axis direction, and the width direction of the deformable substrate is the Y-axis direction; and the magnetoresistive bridge stress sensor comprises a plurality of magnetoresistance sensor units, each of which comprises a multi-film layer stacked structure parallel to a plane X-Y, and the multi-film layer at least comprises a pinning layer, a reference layer, a barrier layer, a free layer, and a bias layer that are stacked in sequence.

4. The hydrogen gas sensor according to claim 3, wherein the deformable substrate has a first surface and a second surface which are arranged along the Z-axis direction;
   the magnetoresistive bridge stress sensor has a push-pull bridge structure, and comprises push magnetoresistance sensor units and pull magnetoresistance sensor units;
   the push magnetoresistance sensor units are disposed on the first surface, and the pull magnetoresistance sensor units are disposed on the second surface; and the push magnetoresistance sensor units and the pull magnetoresistance sensor units bear stresses of the same magnitude and in the opposite directions.

5. The hydrogen gas sensor according to claim 4, wherein the angle at which the initial magnetic moment of the free layer of each push magnetoresistance sensor unit deviates from the Y-axis is α;
   when the magnetic moments of the free layers of the push magnetoresistance sensor units and the magnetic moments of the free layers of the pull magnetoresistance sensor units are simultaneously rotated clockwise or counterclockwise by the same angle to obtain the corresponding magnetic moments of the pinning layers, the angle at which the initial magnetic moment of the free layer of each pull magnetoresistance sensor unit deviates from the Y-axis is 90-α or 270-α; or,
   when the magnetic moments of the free layers of the push magnetoresistance sensor units and the magnetic moments of the free layers of the pull magnetoresistance sensor units are rotated in different directions and by the same angle, the angle at which the initial magnetic moment of the free layer of each pull magnetoresistance sensor unit deviates from the Y-axis is 90+α or 270+α; and
   the value range of α is from 0° to 360°,
   wherein when the free layers are made of a material with a positive magnetostriction coefficient and bear a tensile stress or made of a material with a negative magnetostriction coefficient and bear a compressive stress, α is not 0° or 180°, and when the free layers are made of a material with a positive magnetostriction coefficient and bear a compressive stress or made of a material with a negative magnetostriction coefficient and bear a tensile stress, α is not 90° or 270°.

6. The hydrogen gas sensor according to claim 3, wherein the deformable substrate has a first surface and a second surface which are arranged along the Z-axis direction;
   the magnetoresistive bridge stress sensor has a push-pull bridge structure, and comprises push magnetoresistance sensor units and pull magnetoresistance sensor units;
   the push magnetoresistance sensor units and the pull magnetoresistance sensor units are disposed on the first surface or the second surface at the same time; and the push magnetoresistance sensor units and the pull magnetoresistance sensor units bear stresses of the same magnitude and in the same direction.

7. The hydrogen gas sensor according to claim 6, wherein the angle at which the initial magnetic moment of the free layer of each push magnetoresistance sensor unit deviates from the Y-axis is $\alpha$;

when the magnetic moments of the free layers of the push magnetoresistance sensor units and the magnetic moments of the free layers of the pull magnetoresistance sensor units are simultaneously rotated clockwise or counterclockwise by 90° to obtain the corresponding magnetic moments of the pinning layers, the angle at which the initial magnetic moment of the free layer of each pull magnetoresistance sensor unit deviates from the Y-axis is 180-$\alpha$ or 360-$\alpha$; or, when the magnetic moments of the free layers of the push magnetoresistance sensor units and the magnetic moments of the free layers of the pull magnetoresistance sensor units are rotated in different directions and by the same angle, the angle at which the initial magnetic moment of the free layer of each pull magnetoresistance sensor unit deviates from the Y-axis is $\alpha$ or 180+$\alpha$; and the value range of $\alpha$ is from 0° to 360°, wherein when the free layers are made of a material with a positive magnetostriction coefficient and bear a tensile stress or made of a material with a negative magnetostriction coefficient and bear a compressive stress, $\alpha$ is not 0° or 180°, and when the free layers are made of a material with a positive magnetostriction coefficient and bear a compressive stress or made of a material with a negative magnetostriction coefficient and bear a tensile stress, $\alpha$ is not 90° or 270°.

8. The hydrogen gas sensor according to claim 3, further comprising: a non-hydrogen sensing layer in the same layer as the hydrogen sensing layer; wherein the cantilever beam comprises a fixed part and a reference cantilever beam and a sensing cantilever beam which are respectively disposed at the two sides of the fixed part, the reference cantilever beam is provided with a reference area, and the sensing cantilever beam is provided with a sensing area; or, the membrane assembly comprises a reference membrane and a sensing membrane which are enclosed in the frame, the reference membrane is provided with a reference area, and the sensing membrane is provided with a sensing area; and the hydrogen sensing layer is disposed on the magnetic shielding layer within the sensing area, and the non-hydrogen sensing layer is disposed on the magnetic shielding layer within the reference area.

9. The hydrogen gas sensor according to claim 8, wherein the reference area and the sensing area of the deformable substrate are located on the same plane;

the magnetoresistive bridge stress sensor has a reference bridge structure, and comprises reference magnetoresistance sensor units and sensing magnetoresistance sensor units; and the reference magnetoresistance sensor units are disposed in the reference area, and the sensing magnetoresistance sensor units are disposed in the sensing area.

10. The hydrogen gas sensor according to claim 9, wherein the angle at which the initial magnetic moment of the free layer of each reference magnetoresistance sensor unit deviates from the Y-axis is $\alpha$, and the angle at which the initial magnetic moment of the free layer of each sensing magnetoresistance sensor unit deviates from the Y-axis is $\alpha$;

the magnetic moments of the free layers of the reference magnetoresistance sensor units and the magnetic moments of the free layers of the sensing magnetoresistance sensor units are simultaneously rotated clockwise or counterclockwise by the same angle to obtain the corresponding magnetic moments of the pinning layers; and the value range of $\alpha$ is from 0° to 360°, wherein when the free layers are made of a material with a positive magnetostriction coefficient and bear a tensile stress or made of a material with a negative magnetostriction coefficient and bear a compressive stress, $\alpha$ is not 0° or 180°, and when the free layers are made of a material with a positive magnetostriction coefficient and bear a compressive stress or made of a material with a negative magnetostriction coefficient and bear a tensile stress, $\alpha$ is not 90° or 270°.

11. The hydrogen gas sensor according to claim 1, wherein the magnetoresistive bridge stress sensor is provided with an electrical transmission port assembly, and the electrical transmission port assembly is directly connected with the deformable substrate and is sealed on the deformable substrate by means of sealant.

12. The hydrogen gas sensor according to claim 1, wherein the hydrogen sensing layer comprises at least one of $AB_5$, $AB_3$, $AB_2$, AB, and $A_2B$ type intermetallic compounds, A represents a strong metal hydride forming element, and B represents a transition metal element.

13. The hydrogen gas sensor according to claim 12, wherein the A can be rare earth metals, Ca, Mg, Zr, or Ti, and the B can be Ni, Co, Fe, Mn, or Cr.

* * * * *